United States Patent
Kaplan et al.

(10) Patent No.: US 9,133,103 B2
(45) Date of Patent: Sep. 15, 2015

(54) N-SUBSTITUTED BENZENEPROPANAMIDE AND BENZENEPROPENAMIDE FOR USE IN THE PREVENTION OR THE TREATMENT OF AFFECTIVE DISORDERS

(75) Inventors: Eliahu Kaplan, Petah Tiqwa (IL); Irit Gil-ad, Petah Tiqwa (IL)

(73) Assignee: Novaremed, Ltd., Petah Tiqwa (IL)

( * ) Notice: Subject to any disclaimer, the term of this patent is extended or adjusted under 35 U.S.C. 154(b) by 0 days.

(21) Appl. No.: 14/346,419

(22) PCT Filed: Sep. 10, 2012

(86) PCT No.: PCT/IB2012/054700
§ 371 (c)(1),
(2), (4) Date: May 29, 2014

(87) PCT Pub. No.: WO2013/042005
PCT Pub. Date: Mar. 28, 2013

(65) Prior Publication Data
US 2014/0275273 A1   Sep. 18, 2014

(30) Foreign Application Priority Data
Sep. 21, 2011   (GB) .................................. 1116335.9

(51) Int. Cl.
| | | |
|---|---|---|
| *A01N 37/18* | (2006.01) | |
| *A61K 31/165* | (2006.01) | |
| *C07C 235/34* | (2006.01) | |
| *A61K 47/10* | (2006.01) | |
| *A61K 47/48* | (2006.01) | |
| *C07C 233/22* | (2006.01) | |

(52) U.S. Cl.
CPC ............. *C07C 235/34* (2013.01); *A61K 31/165* (2013.01); *A61K 47/10* (2013.01); *A61K 47/48215* (2013.01); *C07C 233/22* (2013.01)

(58) Field of Classification Search
USPC .................................................. 514/622, 617
See application file for complete search history.

(56) References Cited

FOREIGN PATENT DOCUMENTS

| EP | 1876169 A1 | 1/2008 |
|---|---|---|
| WO | WO-2005110987 A1 | 11/2005 |
| WO | WO-2009109850 A2 | 9/2009 |
| WO | WO-2011030205 A1 | 3/2011 |

*Primary Examiner* — Marcos Sznaidman
(74) *Attorney, Agent, or Firm* — Mintz Levin Cohn Ferris Glovsky and Popeo, P.C.; Shovon Ashraf

(57) ABSTRACT

Compounds for use in the treatment or prophylaxis of an affective disorder, which compound is represented by formula I:

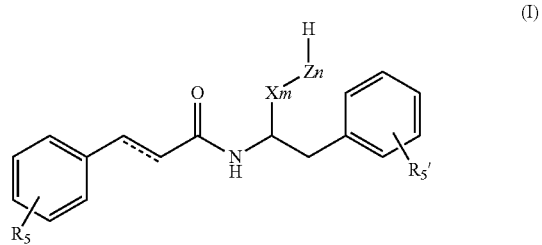

in which:
the dotted line represents a single or a double bond; and $R_5$ and $R_5'$ are independently —H, —OH or —$OR_6$, where $R_6$ is a linear or branched $C_1$-$C_4$ alkyl; X is —$CH_2O$—; Z is —$CH_2CH_2O$—, —$CH(CH_3)CH_2O$— or —$CH_2CH(CH_3)O$—; m is 1; and n is an integer of 1-5; or a pharmaceutically acceptable salt, prodrug, metabolite, or hydrate thereof.

11 Claims, 8 Drawing Sheets

Effect of 135 S (0.1, 5 mg/kg), 175 S (0.1, 5 mg/kg) and Diclofenac (10 mg/kg) (oral, -60, subchronic), in the Open Field on Distance moved [cm] in BALB/c mice [20 min]

Effect of 135 S (0.1, 5 mg/kg), 175 S (0.1, 5 mg/kg) and Diclofenac (10 mg/kg) (oral, -60, subchronic), in the Open Field on Velocity [cm/s] in BALB/c mice [20 min]

Effect of 135 S (0.1, 5 mg/kg), 175 S (0.1, 5 mg/kg) and Diclofenac (10 mg/kg) (oral, -60, subchronic), in the Open Field on Strong mobility [30%] in BALB/c mice [20 min]

Effect of 135 S (0.1, 5 mg/kg), 175 S (0.1, 5 mg/kg) and Diclofenac (10 mg/kg) (oral, -60, subchronic), in the Open Field on Immobility [10%] in BALB/c mice [20 min]

Ratio of total duration between 2+3 to zone 1 for Balb/c mice with treatment of 135 S (0.1, 5 mg/kg), 175S (0.1, 5 mg/kg) and Diclofenac (10mg/kg)(oral, -60, subchronic)

Total duration in zone for Balb/c mice with treatment of 135 S (0.1, 5 mg/kg), 175S (0.1, 5 mg/kg) and Diclofenac (10mg/kg) (oral, -60, subchronic)

Effect of 135 S (0.1; 0.5 & 2.5 mg/kg),
and Fluoxetine (10 mg/kg) [oral adm., -180], in
the FST on Strong mobility [30%] on BALB/c mice $p=0.06-0.08$ Effect of 135 S (0.1; 0.5 & 2.5 mg/kg),
and Fluoxetine (10 mg/kg) [oral adm., -180], in
the FST on Immobility [10%] on BALB/c mice $p<0.05$ Effect of 135 S (0.1; 0.5 & 2.5 mg/kg),
and Fluoxetine (10 mg/kg) [oral adm., -180], in
the FST on Mobility on BALB/c mice Effect of Fluoxetine 10 mg/kg and 135 S (0.1; 0.5; 2.5 mg/kg),
(-180 min, p.o.) on the Elevated Plus Maze
in open arms with BALB/c mice *Frequency to zone*

Effect of Fluoxetine 10 mg/kg and 135 S (0.1; 0.5; 2.5 mg/kg),
(-180 min, p.o.) on the Elevated Plus Maze
in open arms with BALB/c mice *Total duration*

Effect of Fluoxetine 10 mg/kg and 135 S (0.1; 0.5; 2.5 mg/kg),
(-180 min, p.o.) on the Elevated Plus Maze
in open arms with BALB/c mice *Velocity (cm/s)*

Effect of Fluoxetine 10 mg/kg and 135 S (0.1; 0.5; 2.5 mg/kg),
(-180 min, p.o.) on the Elevated Plus Maze
in open arms with BALB/c mice *Distance moved (cm)*

Marble-Burying Behavior in BALB/c mice after
administration of Fluoxetine 10 mg/kg and
135 S (0.1; 0.5; 2.5 mg/kg), (-180 min, p.o.)

N-SUBSTITUTED BENZENEPROPANAMIDE AND BENZENEPROPENAMIDE FOR USE IN THE PREVENTION OR THE TREATMENT OF AFFECTIVE DISORDERS

CROSS-REFERENCE TO RELATED APPLICATIONS

This application is a national stage application, filed under 35 U.S.C. §371, of International Application No. PCT/IB2012/054700, filed Sep. 10, 2012 which claims the benefit of provisional application GB1116335.9 filed Sep. 21, 2011, each of which is herein incorporated by reference in its entirety.

The present invention relates to the treatment or prophylaxis of affective disorders such as anxiety and depression and provides a method of treating or preventing affective disorders as well as the use of certain compounds in the manufacture of medicaments for the treatment or prophylaxis of affective disorders in humans and non-human animals.

Affective disorders are psychiatric diseases with multiple aspects, including biological, behavioural, social, and psychological factors. Affective disorders are characterized by changes in mood as the primary clinical manifestation. Such disorders include depression, anxiety, bipolar disorder, post-partum depression, dysthymia, seasonal affective disorder, schizoaffective disorder, panic disorder, eating disorders, obsessive compulsive disorder and post-traumatic stress disorder. In cases where disturbances in mood (depression, anxiety, elation, and excitement) are severe, patients may additionally experience psychotic symptoms.

Major depressive disorder (MDD), bipolar disorders, and anxiety disorders are the most common affective disorders. Such recurrent mood disorders can have devastating long-term effects and the cost of these illnesses in terms of human suffering, productivity and health care is enormous. Affective disorders can result in symptoms ranging from the mild and inconvenient to the severe and life-threatening; the latter account for more than 15% of deaths due to suicide among those with one of the disorders.

Major depressive disorder (MDD), also known as monopolar depression or unipolar affective disorder, is a common, severe, and sometimes life-threatening psychiatric illness. MDD causes prolonged periods of emotional, mental, and physical exhaustion, with a considerable risk of self-destructive behavior and suicide. Major studies have identified MDD as one of the leading causes of work disability and premature death, representing an increasingly worldwide health and economic concern.

Bipolar affective diseases are divided into various types according to the symptoms displayed: Type I (bipolar I, or BPI) and Type II (bipolar II or BPII) disease, cyclothymic disorder, and hypomania disorder. Other names for bipolar affective disease include manic-depressive disorder, cyclothymia, manic-depressive illness (MDI), and bipolar disorder. People with bipolar diseases experience periods of manic (hyper-excitable) episodes alternating with periods of deep depression. Bipolar disorders are chronic and recurrent affective diseases that may have degrees of severity, tending however to worsen with time if not treated. Severe crises can lead to suicidal attempts during depressive episodes or to physical violence against oneself or others during manic episodes. In many patients, however, episodes are mild and infrequent. Mixed states may also occur with elements of mania and depression simultaneously present. Some people with bipolar affective disorders show a rapid cycling between manic and depressive states.

Anxiety disorders are also common psychiatric disorders, and are considered one of the most under-treated and overlooked health problems. Among its common manifestations are panic syndromes, phobias, chronic generalized anxiety disorder, obsessive-compulsive disorder, and post-traumatic disorder. Anxiety disorders are important contributors to other diseases such as hypertension, digestive and eating disorders, and cardiac arrhythmia. Severe anxiety disorders often lead to tobacco addiction, alcohol abuse, and drug abuse.

In addition to suicide, many other deleterious health-related effects of affective disorders are increasingly being recognized. Far from being diseases with purely psychological manifestations, affective disorders are systemic diseases with deleterious effects on multiple organ systems. For example, MDDs represent a major risk factor for both the development of cardiovascular disease, as well as for death after an index myocardial infarction. Furthermore, a recent study, which controlled for physical illness, smoking and alcohol consumption, found that the magnitude of the increased mortality risk conferred by the presence of high depressive symptoms was similar to that of stroke and congestive heart failure.

It is now recognized that, for many patients, the long-term outcome is often much less favorable than previously thought, with incomplete interepisode recovery, and a progressive decline in overall functioning observed. Indeed, according to the Global Burden of Disease Study, mood disorders are among the leading causes of disability worldwide, and are likely to represent an increasingly greater health, societal, and economic problem in the coming years.

Affective disorders are often associated with a reduction in the central nervous system of certain biogenic amine neurotransmitters, such as dopamine, norepinephrine, and serotonin. Thus, many currently available treatments work primarily by raising biogenic amine neurotransmitter levels, by either inhibiting their uptake or preventing their metabolism. Affective disorders are commonly treated with antidepressant medications, including tricyclic antidepressants (TCAs), monoamine oxidase inhibitors (MAOIs), selective serotonin reuptake inhibitors (SSRIs), combined reuptake inhibitors and receptor blockers, serotonin and norepinephrine reuptake inhibitors (SNRIs), norepinephrine and dopamine reuptake inhibitors (NDRIs), and tetracyclic antidepressants.

Currently available drugs for treating affective disorders unfortunately suffer from delayed onset of action, poor efficacy, and a variety of adverse side effects. Furthermore, a large number of individuals remain refractory to currently available therapies. In light of the shortcomings in current approaches, them exists a need for improved compositions and methods for treating affective disorders, particularly symptoms of depression, anxiety, and psychosis.

An object to the present invention is therefore to provide alternative compounds for the treatment or prophylaxis of anxiety or depression. Another object of the present invention is to provide an alternative method for the treatment or prevention of anxiety or depression.

PCT/IB2009/000448 relates to the use of compounds for the treatment of pain. The Examples of this application relate to experiments in which it was noticed that animals which showed a delayed response to hot plate or other stimuli did not exhibit changes in their general motility when tested in an open field test and were not sedated by the compounds. Since most antidepressants (i.e SSRIs and tricyclic agents) show some sedative effect when used at high doses, it was concluded that the analgesic activity induced by the compounds of the application was independent of effects on the central nervous system.

However, the inventors have now surprisingly found, by carrying out an extension of the previous studies that an effect was seen in comparison to control animals in behavioural tests relating to anxiety and depression. The results obtained suggest that the compounds of the invention have a positive involvement in the CNS. This has been supported by PK data obtained at an advanced stage of research. The inventors have therefore now concluded that the compounds of the invention can be used in the treatment of affective disorders such as anxiety and depression and obsessive compulsive disorder.

According to one aspect of the present invention therefore there are provided compounds for use in the treatment or prevention of affective disorders, which compounds may be represented by general formula I below:

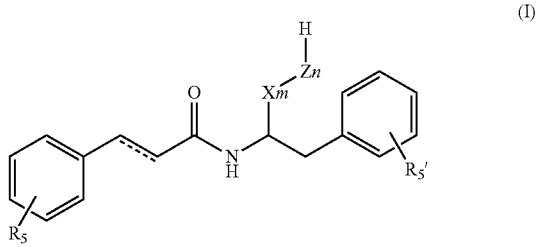

(I)

in which:
the dotted line represents a single or a double bond; and $R_5$ and $R_5'$ are independently —H, —OH or —$OR_6$, where $R_6$ is a linear or branched $C_1$-$C_4$ alkyl;
X is —$CH_2O$—,
Z is —$CH_2CH_2O$—, —$CH(CH_3)CH_2O$— or —$CH_2CH(CH_3)O$—; m is 1; and n is an integer of 1-5, preferably n is 1 or 2.

Suitably, said compounds may be the S-enantiomers of the compounds represented by formula I above. The invention also comprehends the use of the respective pharmaceutically acceptable salts, prodrugs, metabolites, and hydrates of the compounds of formula I.

The term "affective disorder" refers to any type of mood disorder with symptoms including, but not limited to, depression, anxiety, bipolar disorder, post-partum depression, dysthymia, seasonal affective disorder, schizoaffective disorder, panic disorder, eating disorders, obsessive compulsive disorder, post-traumatic stress disorder and disorders induced by alcohol or psychoactive substances such as amphetamine, methamphetamine and cocaine. These disorders are characterized by various symptoms including, but not limited to interference with the ability to work, study, sleep, eat, and enjoy once pleasurable activities.

These disorders are well documented and diagnosis of these disorders is typically accomplished by mental health providers using the Diagnostic and Statistical Manual of Mental Disorders (DSM), published by the American Psychiatric Association, Washington D.C.

The compounds of the present invention may be used for the treatment or prophylaxis of acute or chronic affective disorders. For instance, the compounds may be used for the treatment of depression, anxiety or obsessive compulsive disorder.

The compounds may be used alone or in combination with another anxiolytic or anti-depressant drugs such as phosphodiesterase inhibitors (e.g., PDE3, PDE4, PDE5, PDE7, and PDE10 inhibitors), leukotriene D4 synthesis inhibitors, or other agents effective for treating affective disorders, including but not limited to, antidepressants (such as selective serotonin reuptake inhibitors (SSRIs) e.g. Citalopram, Escitalopram, Fluoxetine, Fluvoxamine, Paroxetine or Sertraline; tricyclic antidepressants (TCAs) e.g. Amitriptyline, Clomipramine, Doxepin, Imipramine, Trimipramine, Desipramine, Nortriptyline, Protriptyline; tetracyclic antidepressants (TeCAs) e.g. Amoxapine, Maprotiline, Mazindol, Mianserin, Mirtazapine, Setiptiline; monoamine oxidase (MAO) inhibitors e.g. Isocarboxazid, Moclobemide, Phenelzine, Selegiline, Tranylcypromine; norepinephrine reuptake inhibitors (NRIs) e.g. Atomoxetine, Mazindol, Reboxetine, Viloxazine; serotonin-norepinephrine reuptake inhibitors (SNRIs) e.g. Desvenlafaxine, Duloxetine, Milnacipran, Venlafaxine; and atypical antidepressants), anxiolytics (such as benzodiazepines e.g. clonazepam, diazepam, estazolam, flunitrazepam, lorazepam, midazolam, nitrazepam, oxazepam, triazolam, temazepam, chlordiazepoxide, alprazolam; agents that enhance gamma-amino butyrate activity; azapirones e.g. buspirone or tandospirone); antipsychotics (such as Haloperidol, Droperidol, Phenothiazines, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Thioxanthenes, Chlorprothixene, Clopenthixol, Flupenthixol, Thiothixene, Zuclopenthixol), tranquilizers, sedatives (such as amobarbital, pentobarbital, secobarbital, phenobarbital), muscle relaxants (such as Carisoprodol, Cyclobenzaprine, Metaxalone, and Methocarbamol), anticonvulsants (such as Gabapentine or Pregabaline), mood stabilisers (such as Valproate, Lithium or Carbamazepine) and insomnia therapeutics (such as benzodiazepines, Zolpidem, Zaleplon, Zopiclone, and Eszopiclone).

According to another aspect of the present invention therefore there is provided a method for treating or preventing affective disorders in a human or non-human animal patient, which method comprises administering to said patient in need thereof a therapeutic effective amount of one or more of the compounds of the invention.

For a human patient, a daily dose of 1.0 mg to 15 g of said one or more compounds in a pure, substantially pure or partially pure form as described in more detail below may suitably be administered. The compounds may be administered under the supervision of a medical practitioner in an amount sufficient to achieve effective management of the anxiety or depression. In some embodiments, the daily dose of said one or more compounds may be titrated to determine such effective amount. Said daily dose may comprise about 5.0 mg to 1 g, typically about 5 mg to 500 mg. In some embodiments, said dose may comprise 10 mg to 100 mg per day of said one or more compounds. The compounds may be administered on a regimen of one to four times per day.

Said one or more compounds may be administered parenterally, transdermally, intramuscularly, intravenously, intradermally, intranasally, subcutaneously, intraperitoneally, intraventricularly or rectally. Preferably, the one or more compounds are administered orally.

Optionally, the one or more compounds of the present invention may be administered simultaneously, sequentially or separately with at least one other antidepressant or anxiolytic medicament.

In yet another aspect of the present invention there is provided the use of one or more of the compounds of the invention in the manufacture of a medicament for use in the treatment or prophylaxis of anxiety or depression. Said medicament may be manufactured for co-administration with one or more other anxiolytic or anti-depressant drugs As mentioned above, n may be 1 to 5, preferably 1 to 2.

In some embodiments of the invention, the compounds of the invention may be represented by general formula II below:

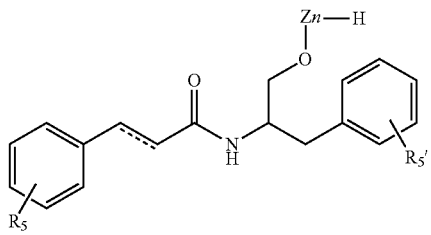
(II)

in which n, Z, $R_5$ and $R_5'$ are as defined above.
Z may be —$CH_2CH(CH_3)O$—.
Z may be —$CH(CH_3)CH_2O$—.

In some embodiments of the present invention, the compounds of the invention may therefore be represented by general formula III below:

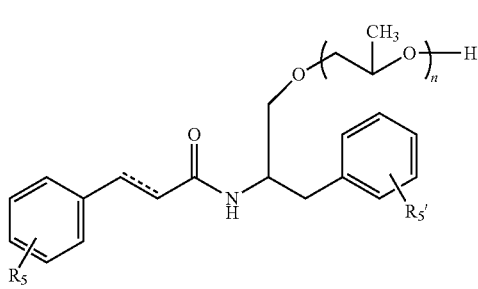
(III)

in which n, $R_5$ and $R_5'$ are as defined above.
$R_5$ may be H. Alternatively, $R_5$ may be OH.
$R_5'$ may be H. Alternatively, $R_5'$ may be OH.

Suitably, n may be an integer from 1-5, preferably 1-3, more preferably 1-2. For example, n may be 1, 2, 3, 4 or 5. Advantageously, n may be 1-2, e.g., 1.

Alternatively, the compounds of the invention may be the S-enantiomers of the compounds represented by general formulae IV, V, VI and VII below:

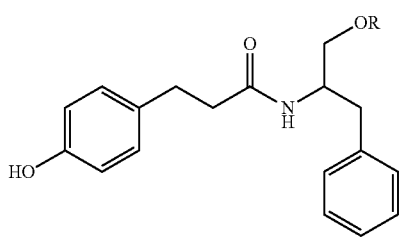
(IV)

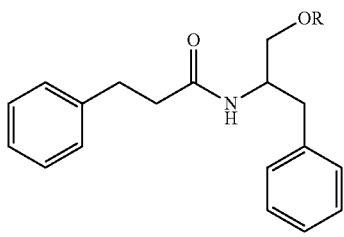
(V)

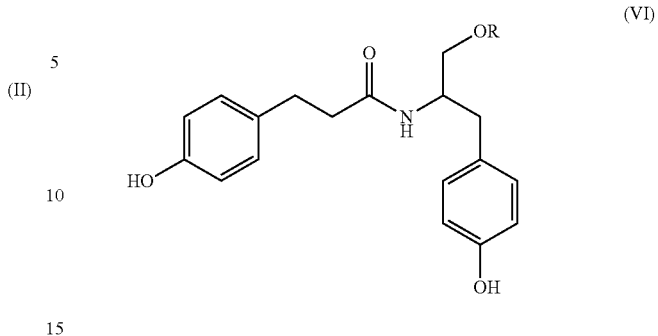
(VI)

(VII)
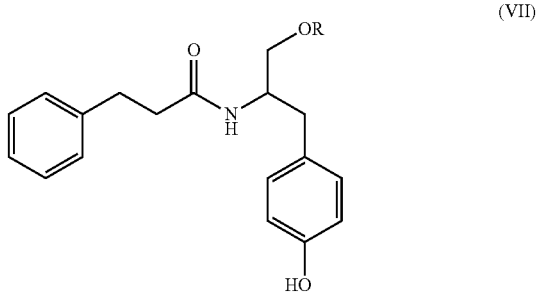

in which R is a polyalkylene glycol polymer having n units, wherein n is as defined above, particularly n=1-5.

Suitably, said polyalkylene glycol polymer may be polyisopropylene glycol.

In a preferred aspect, the compounds of the invention are a compound of formula VII, more preferably a compound having one of the following formulas.

Compound 1

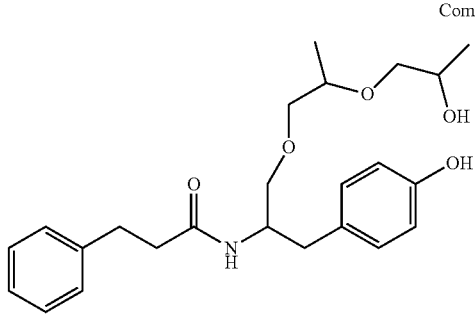
(NRD 71)

Compound 2

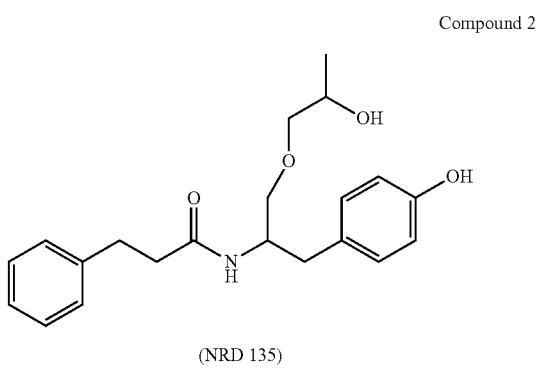
(NRD 135)

Compound 3
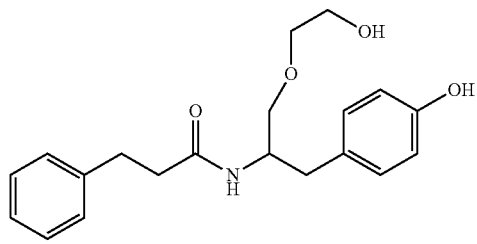
(NRD 175)
All chiral, diastereomeric, racemic, and geometric isomeric forms of a structure are intended, unless specific stereochemistry or isomeric form is specifically indicated. For example, for compound 2, the following isomeric forms are intended:
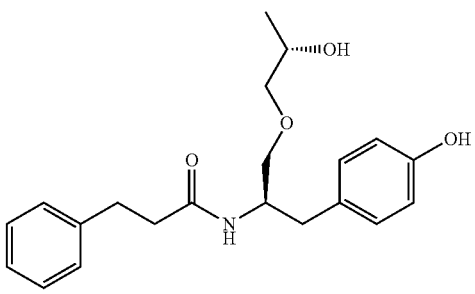
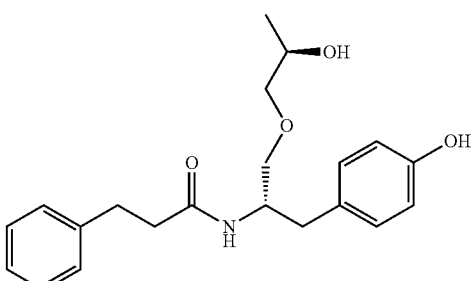
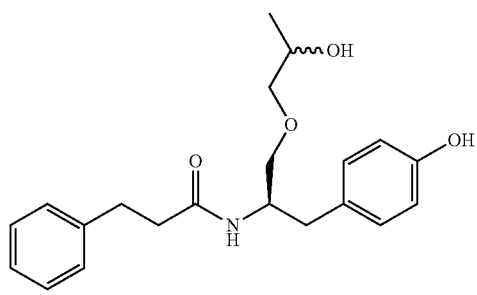
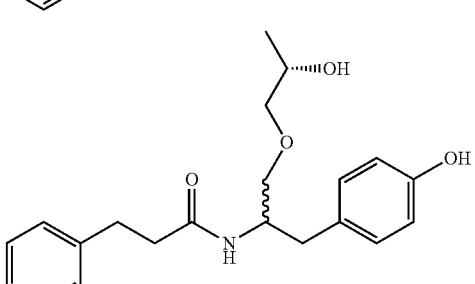
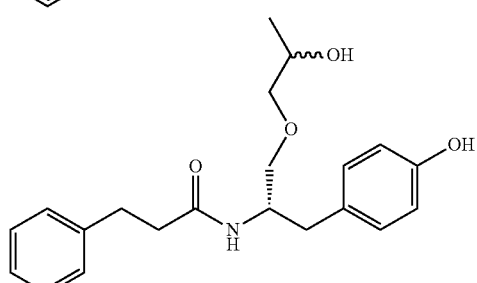
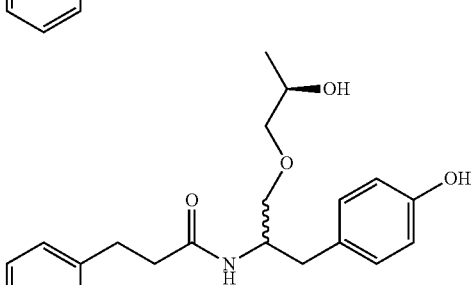
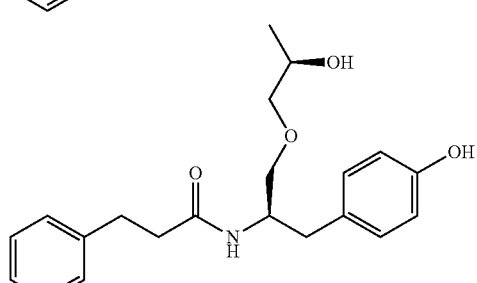
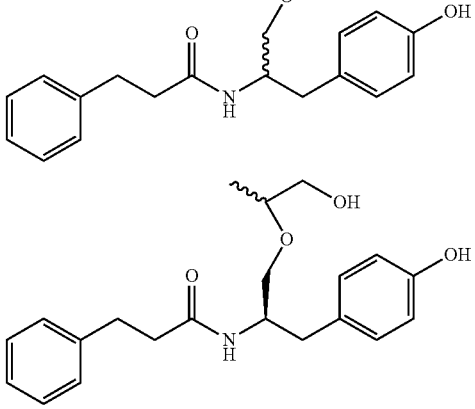
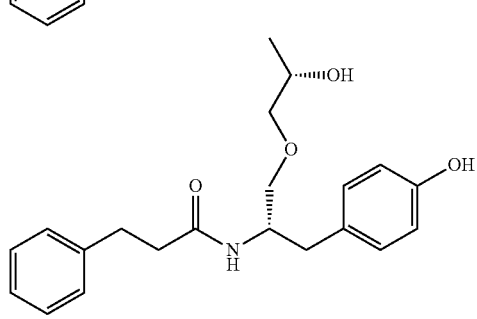
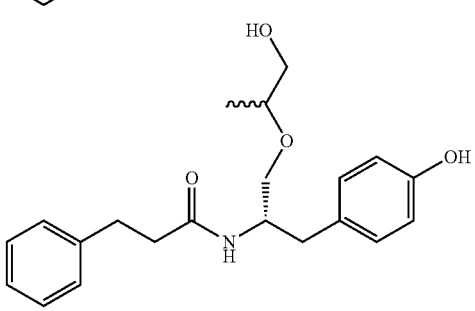
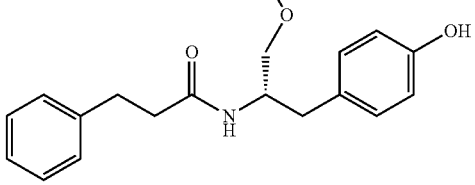

-continued
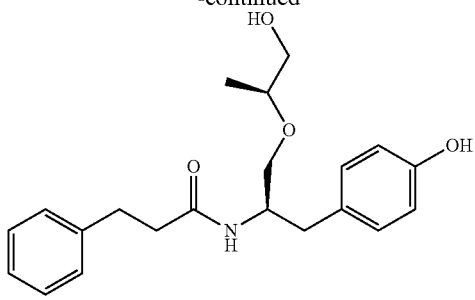
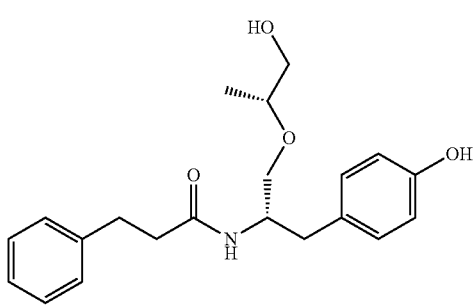
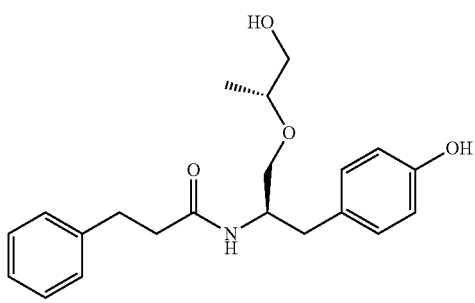
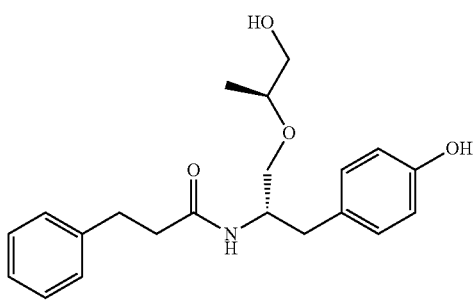
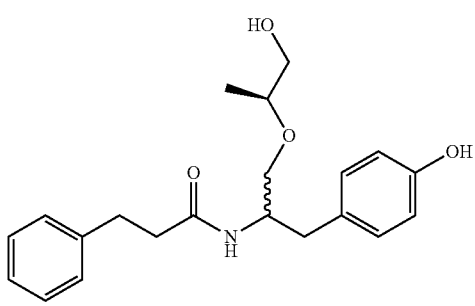
-continued
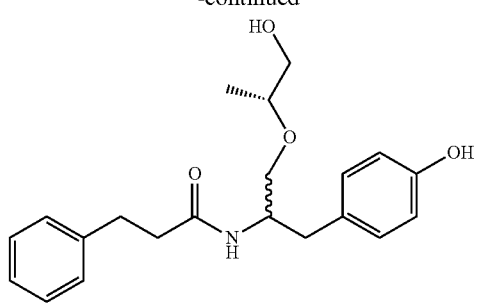
Examples of some isomeric forms of compound 1 are shown below:
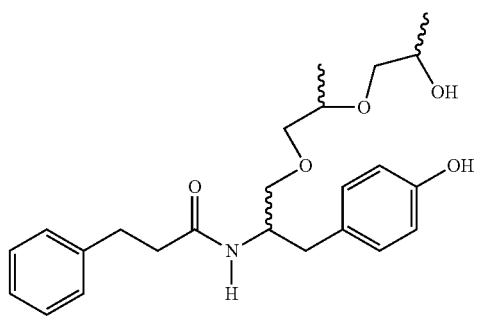
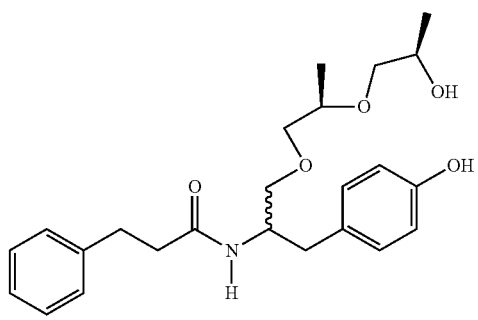
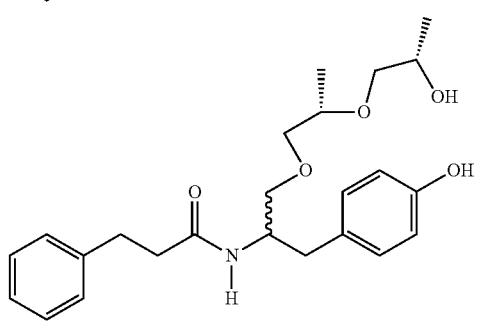
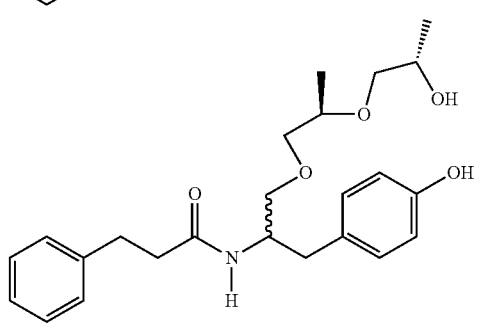

11
-continued
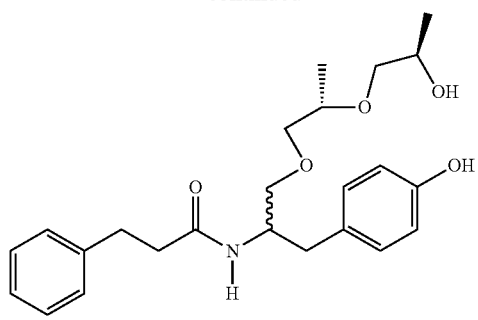
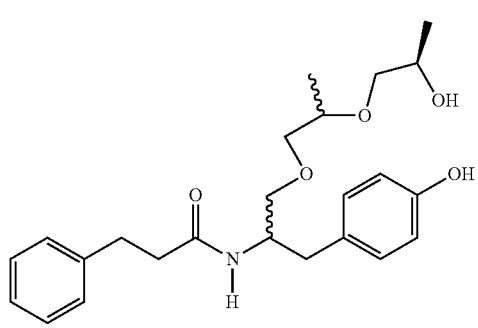
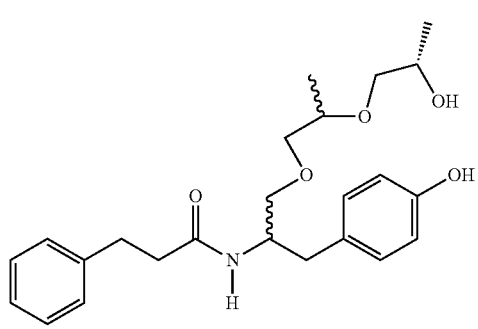
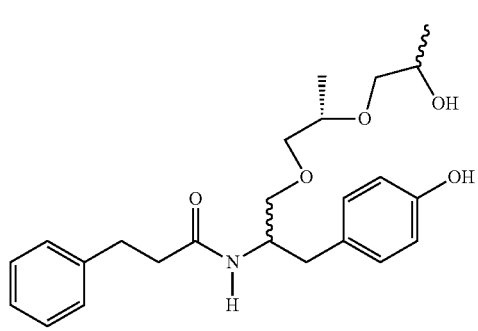
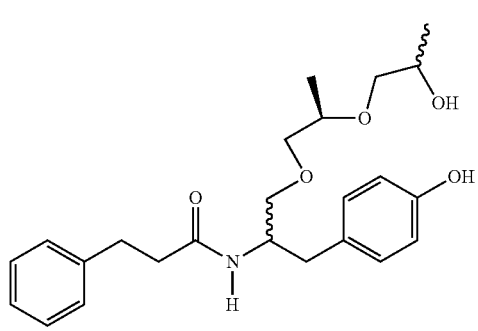
12
-continued
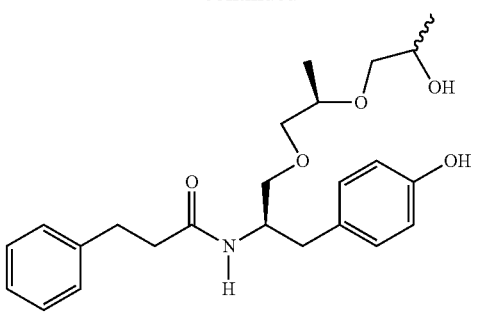
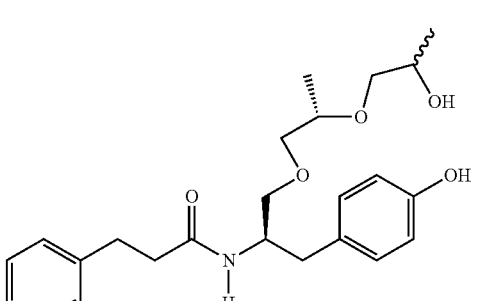
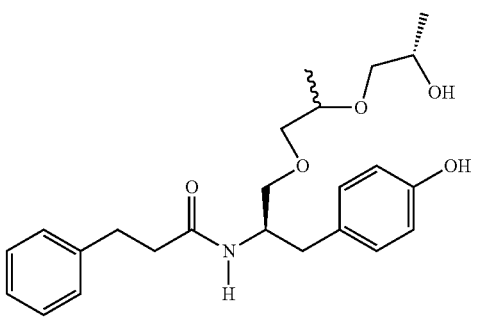
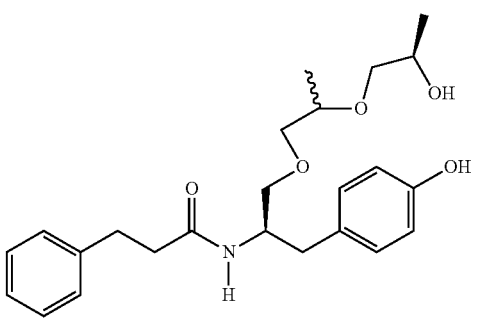
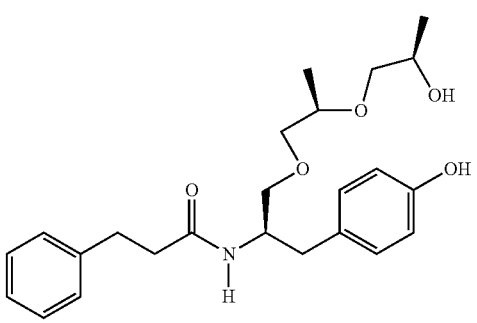

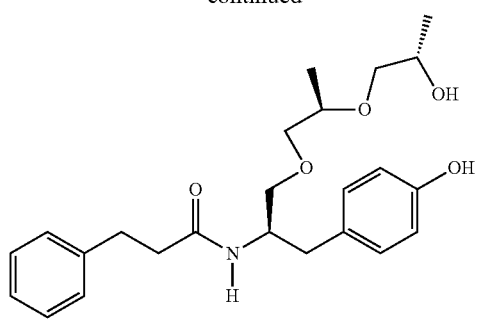
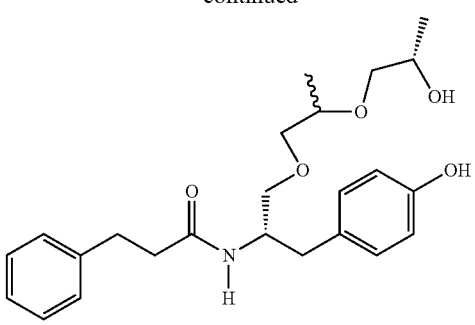

-continued

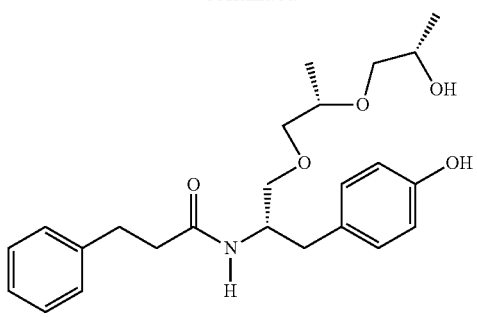

Isomeric forms of compound 1 also include geometric isomers as shown below, including all R and S permutations:

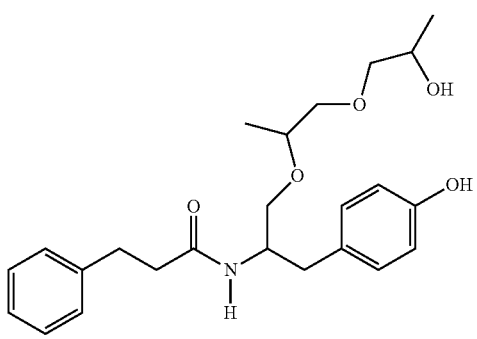

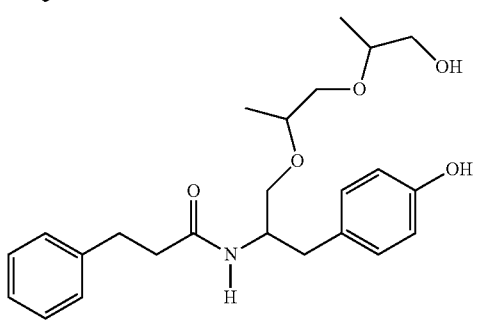

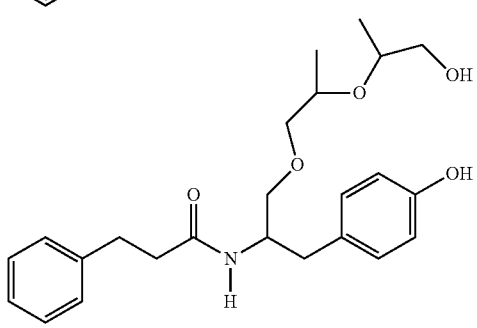

For example, some isomeric forms of compound 3 (NRD 175) are shown below:

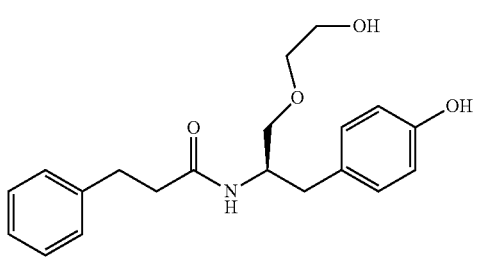

-continued

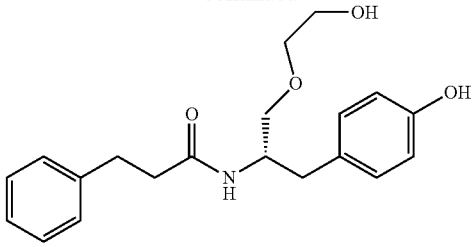

Suitable synthetic methods for obtaining and purifying the compounds of the present invention are disclosed in detail below. However, it should be apparent to a person skilled in the art that the compounds may be prepared using any other feasible synthetic methods.

The compounds of the invention may be synthesised as polyalkylene glycol (PAG) conjugates. Polymers that may be used for such conjugation include poly(ethylene glycol) (PEG), also known as or poly(ethylene oxide) (PEO) and polypropylene glycol (including poly isopropylene glycol).

A polyalkylene glycol (PAG), such as PEG, is a linear polymer terminated at each end with hydroxyl groups:

$$HO-CH_2CH_2O-(CH_2CH_2O)_p-CH_2CH_2-OH.$$

The above polymer, α,ω-dihydroxyl poly(ethylene glycol), can also be represented as HO-PEG-OH, where it is understood that the -PEG-symbol represents the following structural unit:

$$-CH_2CH_2O-(CH_2CH_2O)_p-CH_2CH_2-$$

where p may range from 0 to about 48. PEG may be used as methoxy-PEG-OH, or mPEG, in which one terminus is the relatively inert methoxy group, while the other terminus is a hydroxyl group that is subject to ready chemical modification. Additionally, random or block copolymers of different alkylene oxides (e.g., ethylene oxide and propylene oxide) that are closely related to PEG in their chemistry may be substituted for PEG.

The PAG polymers may be linear or branched.

It is to be understood that compounds of the invention comprise a PAG moiety that may include a mixture of polymers which have a varying number of monomeric units. The synthesis of a PAG-conjugate compound may produce a population of molecules with a Poisson distribution of the number of monomeric units per polymer in the conjugate. Thus, a compound according to the invention that is described as having a polymer of n=2 monomeric units refers not only to the actual polymers in that population being described as having n=2 monomeric units, but also to a population of molecules with the peak of the distribution being 2 or close to 2. The distribution of monomeric units in a given population can be determined, e.g., by nuclear magnetic resonance (NMR) or by mass spectrometry (MS).

In yet another aspect of the present invention there is provided a pharmaceutical composition for use in the treatment or prophylaxis of anxiety or depression, said composition comprising a pharmaceutically effective amount of one or more of the compounds of the invention. Said composition may further comprise one or more pharmaceutically acceptable excipients. In some embodiments, said composition may also comprise another anxiolytic or anti-depressant drugs, such as phosphodiesterase inhibitors (e.g., PDE3, PDE4, PDE5, PDE7, and PDE10 inhibitors), leukotriene D4 synthesis inhibitors, or other agents effective for treating affective disorders, including but not limited to, antidepressants, antipsychotics, tranquilizers, sedatives, muscle relaxants, anticonvulsants, and insomnia therapeutics.

"Other anxiolytic or anti-depressant agents" include glial attenuators, such as Minocycline, Fluorocitrate, MWO 1-5-188WH, Propentofylline (also a PDE inhibitor), Pentoxyfylline (also a PDE inhibitor), Rolipram (also a PDE inhibitor), IL-10, IL-1 receptor antagonist(s), TNF-receptor antagonist(s) including sTNFR, MAP-kinase inhibitor(s), Yohimbine, glial cell chloride antagonists, caspase inhibitors, MMP inhibitors, cannabinoid receptor (e.g., type 2) agonists, arundic acid, statins, thalidomide and related analogs; phosphodiesterase inhibitors, such as Rolipram, Arofylline, Doxofylline, Cipamfylline, Roflumilast, Tetomilast, Atizoram, CC-1088, Tofimilast, Tolafentrine, Pentoxyfylline, Dipyridamole, Cilostazol, Theophylline, Cilomilast, AWE-12-28, Propentofylline; antidepressants, such as tricyclic antidepressants, including but not limited to, amitriptyline, amoxapine, desipramine (Norpramin®), doxepin (Sinequan®), imipramine (Tofranil®), nortriptyline (Pamelor®), protriptyline (Vivactil®), and trimipramine (Surmontil®); monoamine oxidase inhibitors, including but not limited to, isocarboxazid, pargyline, selegiline, furazolidone and phenelzine; selective serotonin reuptake inhibitors, including but not limited to, citalopram (Celexa®), escitalopram (Cipralex®), fluoxetine (Prozac®, Prozac Weekly®), paroxetine (Paxil®, Paxil CR®), sertraline (Zoloft®); combined reuptake inhibitors and receptor blockers, including but not limited to, trazodone, nefazodone, and maprotiline; serotonin and norepinephrine reuptake inhibitors, including but not limited to, duloxetine (Cymbalta®) and venlafaxine (Effexor, Effexor XR®); norepinephrine and dopamine reuptake inhibitors, including but not limited to, bupropion (Wellbutrin®, Wellbutrin SR®, Wellbutrin XL®); and tetracyclic antidepressants, including but not limited to, Mirtazapine (Remeron®, Remeron SolTab®); benzodiazepines, such as diazepam, chlordiazepoxide, alprazolam, clonazepam, temazepam, lorazepam, flurazepam, oxazepam, clorazepate and triazolam; insomnia therapeutics, such as flurazepam, temazepam, zolpidem tartrate, eszopiclone, diphenhydramine, and doxylamine.

The precise amount of a secondary active agent to be administered during combination therapy will, of course, be adjusted accordingly and will depend upon factors such as intended patient population, the particular affective disorder symptom or condition to be treated, potential synergies between the active agents administered and will readily be determined by one skilled in the art based upon the guidance provided herein.

The pharmaceutical composition of the invention may comprise one or more of the compounds of the invention in a pure, substantially pure or partially pure form. In some embodiments, said substantially pure form may comprise at least 95% wt. of said one or more compounds, e.g., 96% wt., 97% wt., 98% wt. or more than 99% wt. of said compounds.

Said substantially or partially pure form of said compound(s) may further comprise a proportion of free polyalkylene glycol such, for example, as polyethylene glycol (PEG) or polypropylene glycol (PPG). Such polyalkylene glycol may itself be biologically active. The chain length of the free polyalkylene glycol may range from 1-50, preferably 1-25, more preferably 1-5 or 1 or 2. In some embodiments, said polyalkylene glycol may have a chain length of 1, 2, 3 4 or 5 monomeric units. Said free polyalkylene glycol may comprise a mixture of different chain lengths. Thus, for a substantially pure form of said one or more compounds, said form may comprise up to 5% wt. of free polyalkylene glycol, e.g., up to 4% wt., 3% wt., 2% wt. or less than 1% wt., with the total amount in said form of said one or more compounds and said free polyalkylene glycol being 100% wt.

Said partially pure form of said one or more compounds may comprise about 5-60% wt. of the one or more compounds according to the invention and about 95-40% wt. of free polyalkylene glycol, the total amount being 100% wt. Typically, said partially pure form may comprise about 45-55% wt. of said one or more compounds and about 55-45% wt. of said one or more polyalkylene glycols. Alternatively, said form may comprise about 80-95% wt. of said one or more compounds and about 20-5% wt. of said polyalkylene glycol(s).

Suitably, the composition of the invention may be formulated as a unit dosage form. Each unit dosage form may comprise all or a predetermined fraction of the daily dose amount of the one or more compounds of the invention, e.g., one half or one quarter of the daily dose amount.

Thus, the composition may be formulated as a tablet, a pill, a capsule, a powder, granules, a sterile parenteral solution or suspension, a metered aerosol or liquid spray, drops, an ampoule, an auto-injector device, a suppository, a cream or a gel. Said composition may be adapted for oral, enteral parenteral, intrathecal, intranasal, sublingual, rectal or topical administration, or for administration by inhalation or insufflation. Oral compositions such as tablets, pills, capsules or wafers are particularly preferred.

For preparing a solid dosage form such as a tablet, said one or more compounds may be mixed with one or more pharmaceutical excipients, e. g., conventional tabletting ingredients such as corn starch, lactose, sucrose, sorbitol, talc, stearic acid, magnesium stearate, dicalcium phosphate or gums, or other pharmaceutical diluents, e. g., water, to form a solid pre-formulation composition containing a substantially homogeneous mixture of said one or more compounds, such that said one or more compounds are dispersed evenly throughout the composition, so that the composition may be readily subdivided into equally effective unit dosage forms such as tablets, pills and capsules.

Said solid pre-formulation composition is then subdivided into unit dosage forms of the kind mentioned above which may each contain from 0.1 to about 500 mg of the one or more compounds. Favoured unit dosage forms contain from 1 to 500 mg, e.g., 1, 5, 10, 25, 50, 100, 300 or 500 mg, of the compound(s).

When formulated as a tablet or pill, said tablet or pill may be coated or otherwise compounded to provide a dosage form affording the advantage of prolonged action. For instance, said tablet or pill can comprise an inner dosage and an outer dosage component, the latter being in the form of an envelope over the former. These two components may be separated by an enteric layer that serves to resist disintegration in the stomach and permits the inner component to pass intact into the duodenum or to be delayed in release. A variety of materials are known in the use in such enteric layers or coatings, such materials including a number of polymeric acids and mixtures of polymeric acids with such materials as shellac, cetyl alcohol and cellulose acetate.

Alternatively, the pharmaceutical composition of the present invention may be formulated as a liquid dosage form for administration orally or by injection; for example an aqueous solution, a suitably flavoured syrup, an aqueous or oil suspension or a flavoured emulsion with edible oils such, for example, as cottonseed oil, sesame oil, coconut oil or peanut oil, as well as an elixir or a similar pharmaceutical vehicle. Suitable dispersing or suspending agents for an aqueous suspension include synthetic and natural gums, e.g., tragacanth, acacia, alginate, dextran, sodium carboxymethylcellulose, methylcellulose, polyvinyl-pyrrolidone or gelatin.

The following is a description by way of example only with reference to the accompanying drawings of embodiments of the present invention.

Figure 1A:
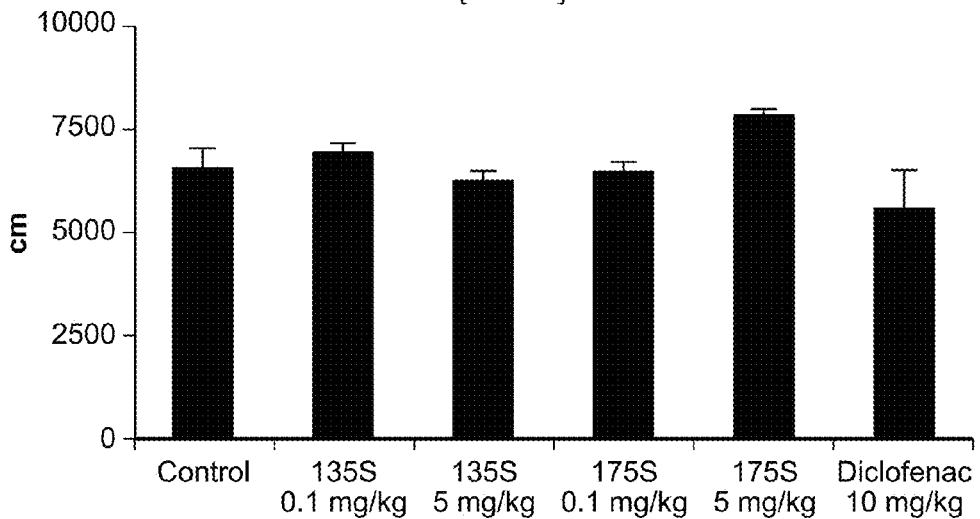
FIG. 1A shows the effect of 135S (0.1, 5 mg/kg), 175S (0.1, 5 mg/kg) and Diclofenac (10 mg/kg) (oral, −60, subchronic) in an open field test on distance moved (cm) in Balb/c mice over a period of 20 minutes.
Figure 1B:
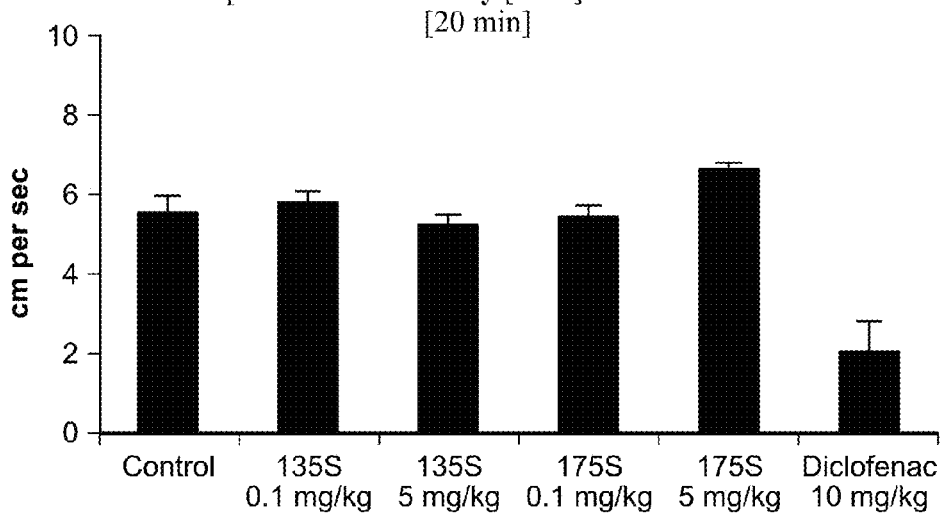
FIG. 1B shows the effect of 135S (0.1, 5 mg/kg), 175S (0.1, 5 mg/kg) and Diclofenac (10 mg/kg) (oral, −60, subchronic) in an open field test on velocity (cm/sec) in Balb/c mice over a period of 20 minutes.
Figure 1C:
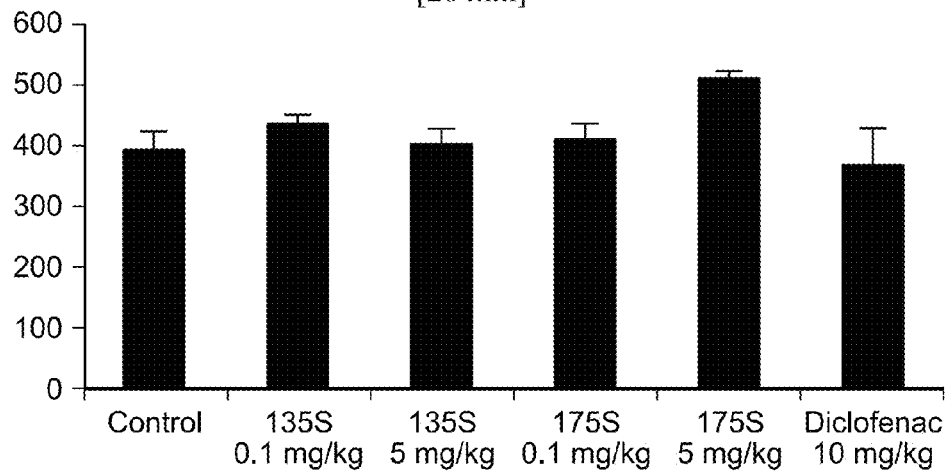
FIG. 1C shows the effect of 135S (0.1, 5 mg/kg), 175S (0.1, 5 mg/kg) and Diclofenac (10 mg/kg) (oral, −60, subchronic) in an open field test on strong mobility (30%) in Balb/c mice over a period of 20 minutes.
Figure 1D:
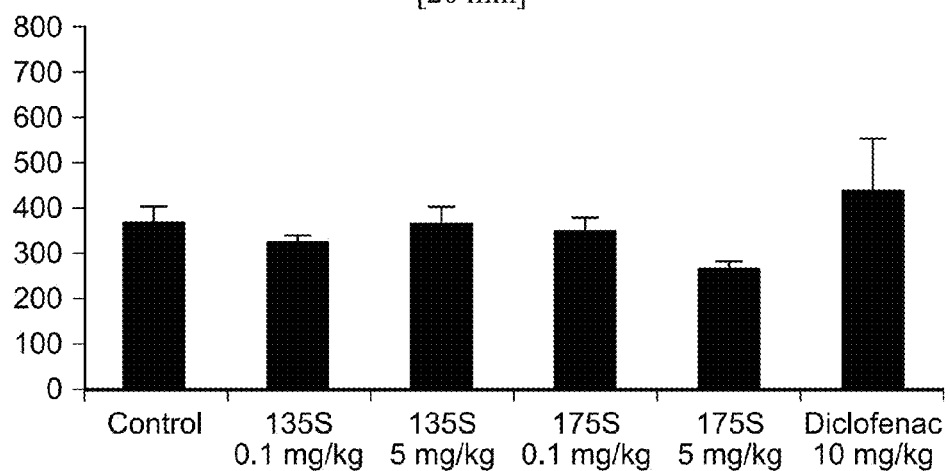
FIG. 1D shows the effect of 135S (0.1, 5 mg/kg), 175S (0.1, 5 mg/kg) and Diclofenac (10 mg/kg) (oral, −60, subchronic) in an open field test on immobility (10%) in Balb/c mice over a period of 20 minutes.
Figure 1E:
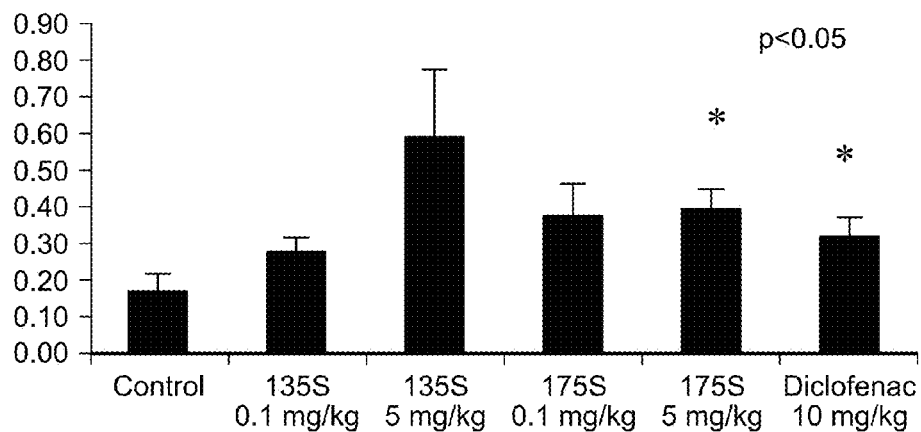

FIG. 1E shows the ratio of total duration between zones 2 and 3 compared with zone 1 for Balb/c mice following treatment with 135S (0.1, 5 mg/kg), 175S (0.1, 5 mg/kg) and Diclofenac (10 mg/kg) (oral, −60 subchronic).

Figure 1F:
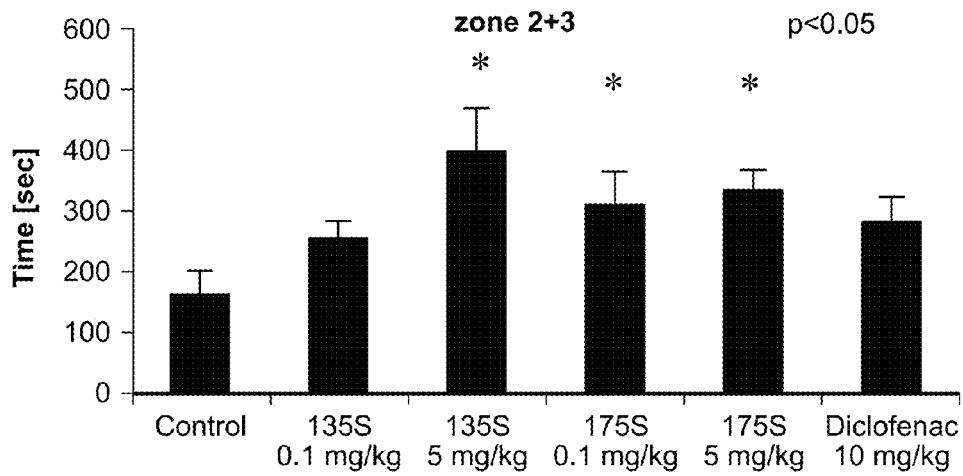

FIG. 1F shows the total duration (seconds) in zones 2 and 3 for Balb/c mice with treatment of 135S (0.1, 5 m mg/kg), 175S (0.1, 5 mg/kg) and Diclofenac (10 mg/kg) (oral, −60 subchronic).

Figure 2A:
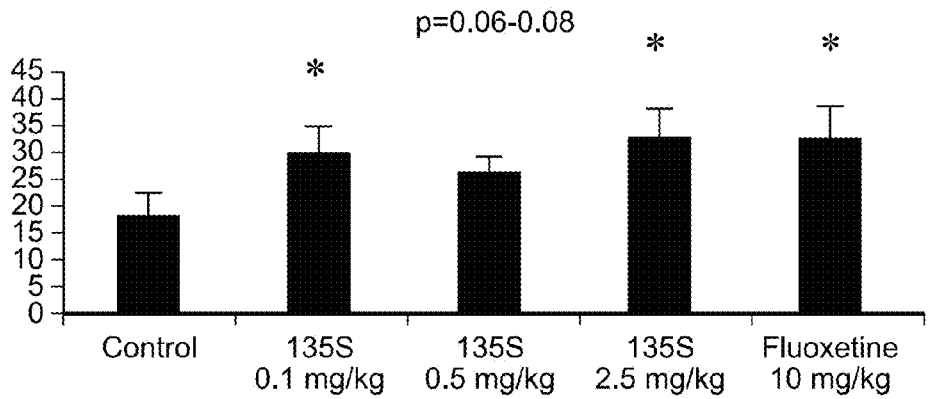

FIG. 2A shows the effect of 135S (0.1, 0.5 and 2.5 mg/kg) and Fluoxetine (10 mg/kg) (oral, −180) in the forced swim test on strong mobility (30%) on Balb/c mice.

Figure 2B:
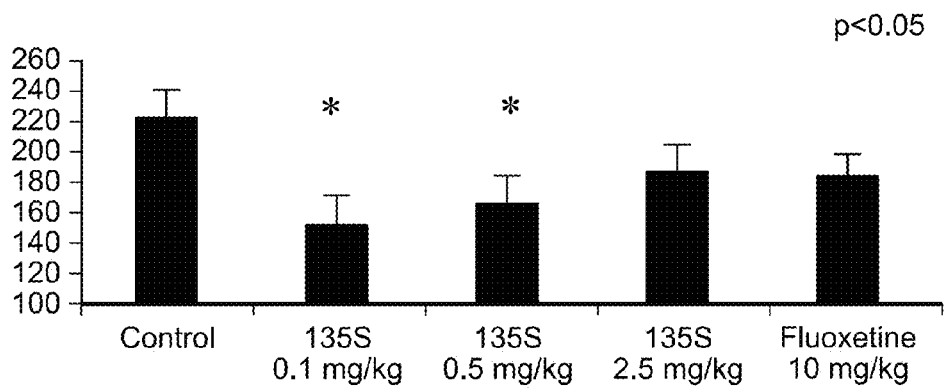

FIG. 2B shows the effect of 135S (0.1, 0.5 and 2.5 mg/kg) and Fluoxetine (10 mg/kg) (oral, −180) in the forced swim test on immobility (10%) on Balb/c mice.

Figure 2C:
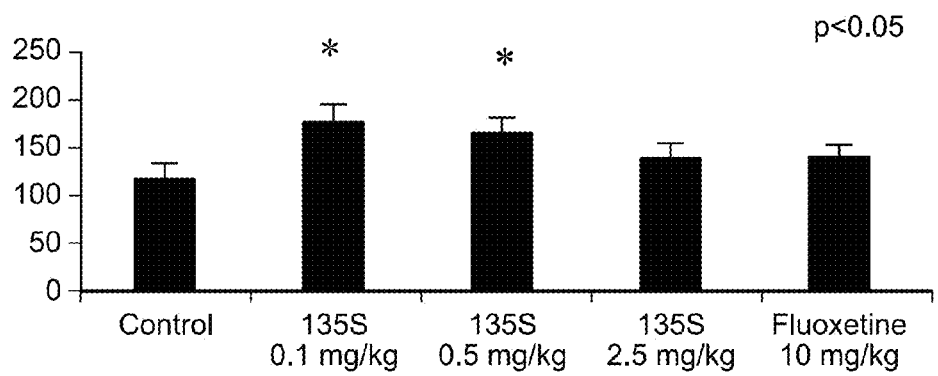

FIG. 2C shows the effect of 135S (0.1, 0.5 and 2.5 mg/kg) and Fluoxetine (10 mg/kg) (oral, −180) in the forced swim test on mobility on Balb/c mice.

Figure 3A:
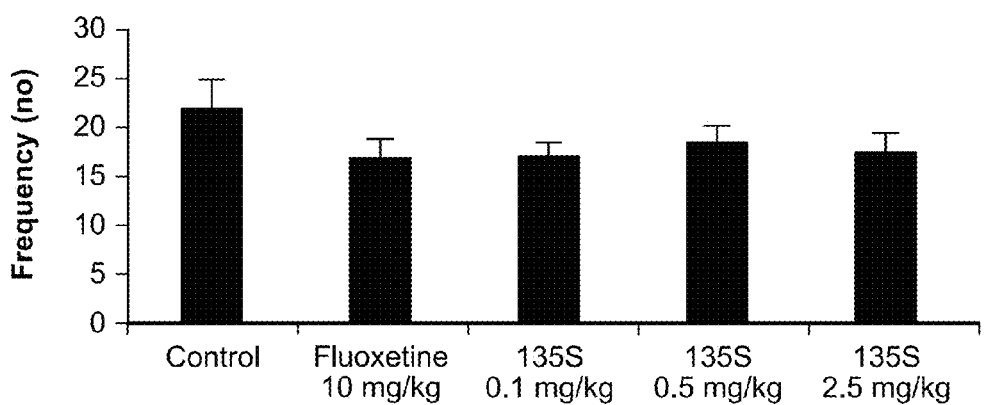

FIG. 3A shows the effect of fluoxetine 10 mg/kg and 135S (0.1, 0.5, 2.5 mg/kg) 9-180 min, p.o.) on the elevated plus maze in open arms with Balb/c mice in relation to the frequency to the open arm zone.

Figure 3B:
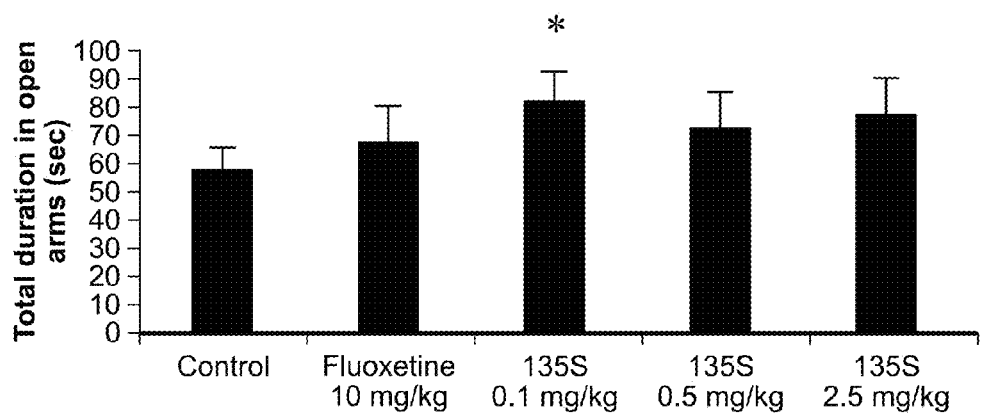

FIG. 3B shows the effect of fluoxetine 10 mg/kg and 135S (0.1, 0.5, 2.5 mg/kg) 9-180 min, p.o.) on the elevated plus maze in open arms with Balb/c mice in relation to the total duration spent in the open arm zone.

Figure 3C:
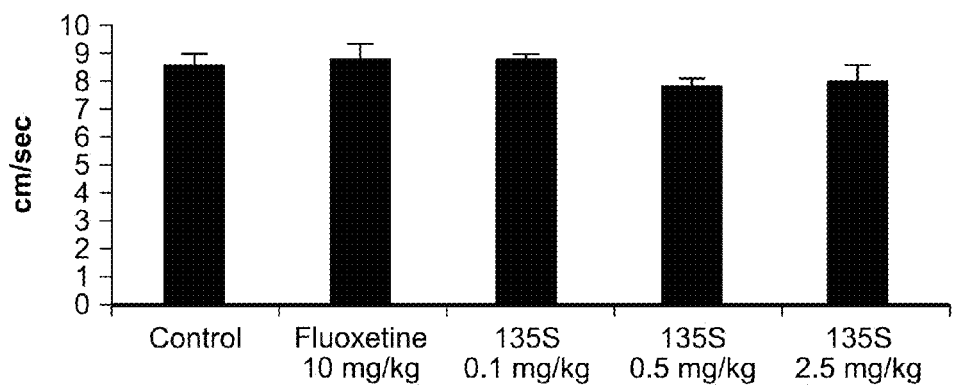

FIG. 3C shows the effect of fluoxetine 10 mg/kg and 135S (0.1, 0.5, 2.5 mg/kg) 9-180 min, p.o.) on the elevated plus maze in open arms with Balb/c mice in relation to the velocity of the mice (cm/sec).

Figure 3D:
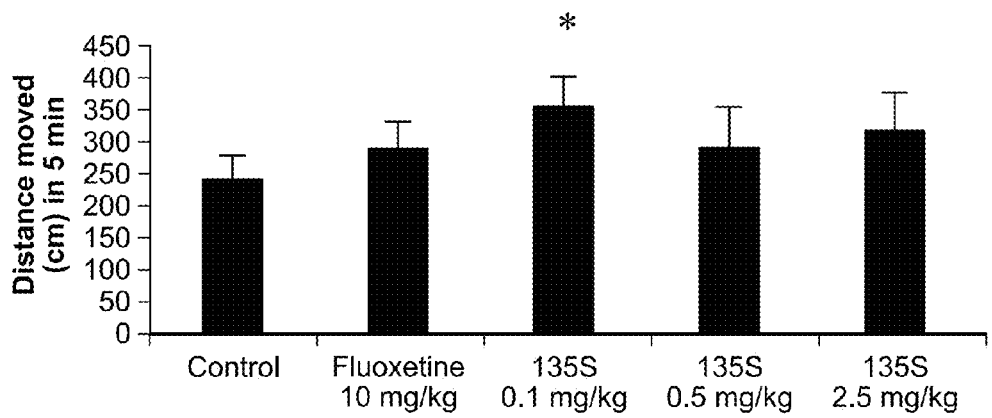

FIG. 3D shows the effect of fluoxetine 10 mg/kg and 135S (0.1, 0.5, 2.5 mg/kg) 9-180 min, p.o.) on the elevated plus maze in open arms with Balb/c mice in relation to the distance moved by the mice (cm).

Figure 4:
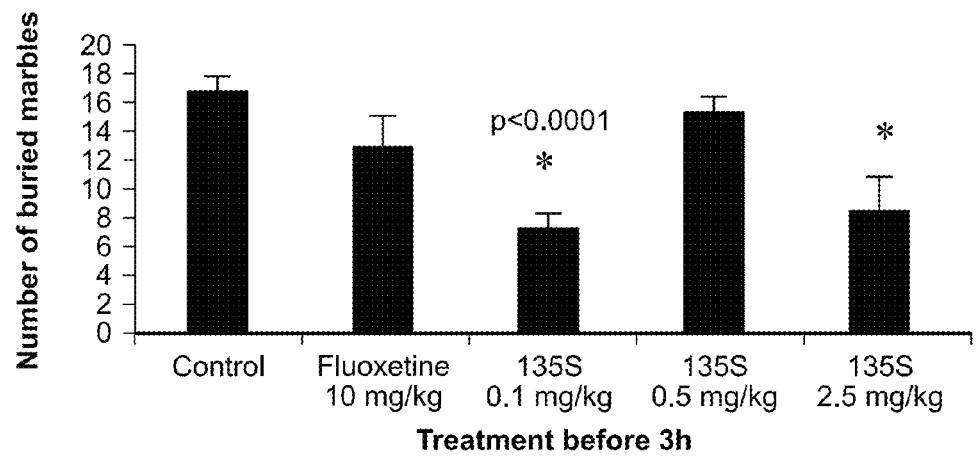

FIG. 4 shows the effect on marble-burying behaviour in Balb/c mice after administration of fluoxetine 10 mg/kg and 135S (0.1, 0.5 and 2.5 mg/kg) (−180 min, p.o).

Figure 5:
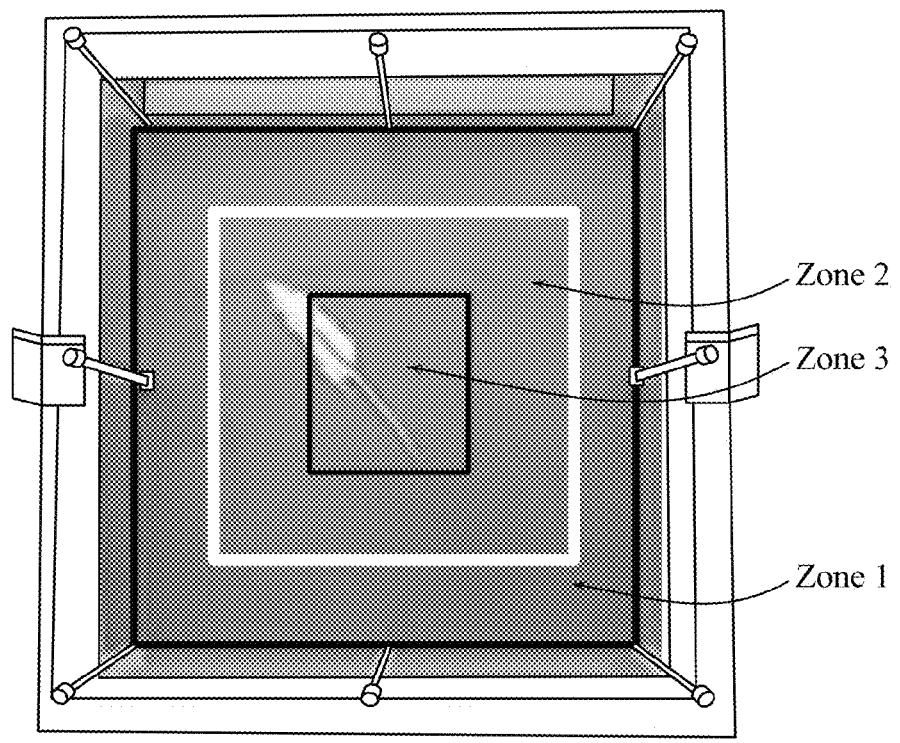

FIG. 5 is a pictorial diagram of an Open field test set up, which tests exploratory locomotor activity.

SYNTHESIS OF POLYALKYLENE GLYCOL COMPOUNDS

Polyalkylene glycol compounds were generally synthesised by preparation of the appropriate alcohol compound followed by conjugation of the alcohol with a polyalkylene glycol (PAG) polymer (e.g., polyethylene glycol (PEG) or polypropylene glycol (PPG)) of the desired length.

Synthesis a: Compound a (Phenyl Alaninol)

1.2 g, 32 mM, of LiAlH$_4$ were added to 2.3 g, 10 mM, phenyl alanine ethyl ester HCl in 50 ml dry ether. After stirring for 2 hours at room temperature, water and KOH were added and the reaction product was extracted with ethyl acetate. After evaporation, 0.8 g of Compound a, a light yellow oil, was obtained.

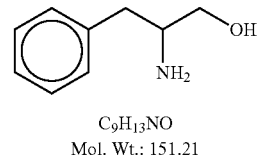

a $C_9H_{13}NO$
Mol. Wt.: 151.21

Compound a crystallised on standing. Mp-70.

NMR CDCl$_3$ 7.30 (5H,m), 3.64 (1H, dd, J=10.5, 3.8 Hz) 3.40 (1H, dd, J=10.5, 7.2 Hz) 3.12 (1H,m), 2.81 (1H, dd, J=13.2, 5.2 Hz), 2.52 (1H, dd, J=13.2, 8.6 Hz).

NMR acetone d$_6$ 7.30 (5H, m), 3.76 (1H, dt) 3.60 (1H, m) 3.30 (11-1, t), 2.85 (2H, m). *Helv. Chim. Acta,* 31, 1617 (1948). Biels.-E3, Vol. 13, p 1757.

Synthesis b: Compound b (Tyrosinol)

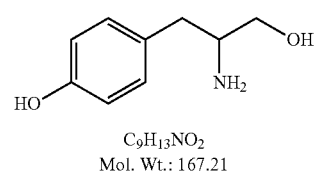

$C_9H_{13}NO_2$
Mol. Wt.: 167.21

To 3 g, 12 mM, L-tyrosine ethyl ester HCl in 50 ml dry ether was added 1.2 g 32 mM LiAlH$_4$. After stirring 3 hours at room temperature, water and KOH were added and the reaction was extracted with ethyl acetate. Evaporation gave 1.1 g of a light yellow oil, 54% yield, which on standing crystallized. mp-85.

NMR CDCl$_3$ 7.20 (4H,AB q, J=8.6 Hz), 3.50 (2H,m) 3.20 (1H,m), 2.81 (2H,m).

NMR tyrosine ethyl ester free base CDCl$_3$ 7.0, 6.56 (4H, AB q, J=8.8 Hz), 4.20 (2H, q, J=7, 0 Hz), 3.70, 3.0, 2.80 (3H, 12 line ABXm), 1.28 (3H, t, J=7.0 Hz). JAGS 71, 305(1949). Biels.-E3, Vol. 13, p 2263.

Synthesis 1: Compound 2

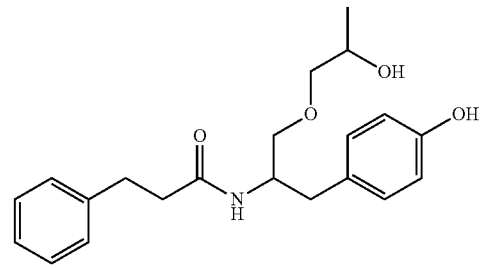 [SMILES: CC(O)COCC(Cc1ccc(O)cc1)NC(=O)CCc1ccccc1]

Compound 2 (NRD 135) has the structure of general formula IV, with R=PPG and n=1. MW=354

Compound 2 was synthesised as follows.

A)i)

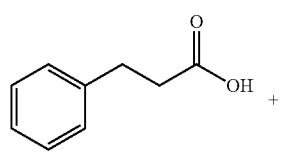

Chemical Formula: C$_9$H$_{10}$O$_2$
Molecular Weight: 150.17
C, 71.98; H, 6.71; O, 21.31
Hydrocinnamic Acid

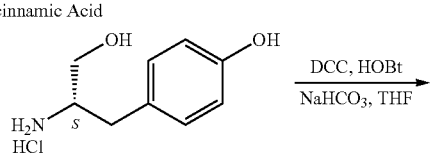

Chemical Formula: C$_9$H$_{14}$ClNO$_2$
Molecular Weight: 203.67
C, 53.08; H, 6.93; Cl, 17.41; N, 6.88; O, 15.71
L-Tyrosinol HCl

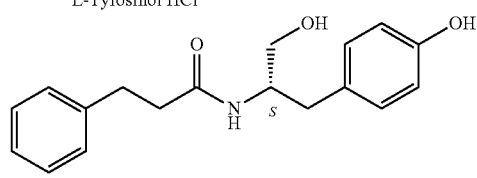

Chemical Formula: C$_{18}$H$_{21}$NO$_3$
Molecular Weight: 299.36
C, 72.22; H, 7.07; N, 4.68; O, 16.03
AV74S 4037-6

L-tyrosinol (24.4 g) was reacted with hydrocinnamic acid (HCA, 1.02 eq), DCC (1.1 eq), HOBT (1.1 eq) and NaHCO$_3$ (4.0 eq) at room temperature overnight. Reaction was completed overnight at RT. The reaction was filtered and a solvent swap from THF to EA was performed. The EA layer was washed with 1N HCl, sat NaHCO$_3$, Brine, and organic layer dried over Na$_2$SO$_4$. Removal of a portion of EA was conducted via distillation, then slow addition of heptane afforded 33.82 g (94.1% yield) of desired product. HPLC: Purity=≥92%.

ii)

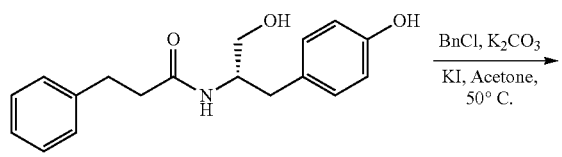

AV74S Tyrosinol Core
299.36 g/mol

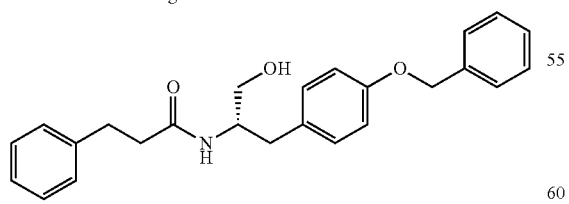

OBn-AV74S Tyrosinol Core
C$_{25}$H$_{27}$NO$_3$
389.49 g/mol

The benzyl ether of AV74S was prepared. 1.33 eq benzyl chloride was charged to AV74S (50.90 g), 1.33 eq potassium carbonate, 0.1 eq potassium iodide in acetone at 50° C. After 20 hours at 50° C., the reaction was heated to reflux for an additional 7 hours to consume all the starting material. The reaction was cooled to room temperature and quenched with water. The slurry was cooled to <5° C. and stirred for 1.5 hours, then filtered. The solids were dried in vacuo (70° C.) over the weekend to afford 62.98 g of crude solids. The AUC purity was 94.4%. $^1$H NMR analysis supports the assigned structure.

B)i)

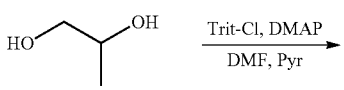

Chemical Formula: C$_3$H$_8$O$_2$
Molecular Weight: 76.09
C, 47.35; H, 10.60; O, 42.05

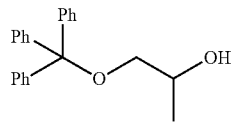

Chemical Formula: C$_{22}$H$_{22}$O$_2$
Moleculare Weight: 318.41
C, 82.99; H, 6.96; O, 10.05

A 5-fold excess of propylene glycol was treated with trityl-Cl (246.7 g, 885 mmol) in the presence of pyridine and DMAP in DMF at rt. The reaction was allowed to stir over the weekend at rt. The mixture was diluted with 3 vol of water and extracted with EA. The recrystallization from acetonitrile/water afforded 235.04 g (83.4% yield, Purity=98.7%) of desired product.

ii)

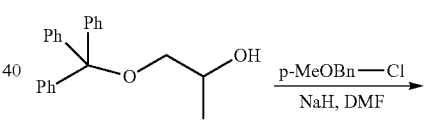

Chemical Formula: C$_{22}$H$_{22}$O$_2$
Moleculare Weight: 318.41
C, 82.99; H, 6.96; O, 10.05

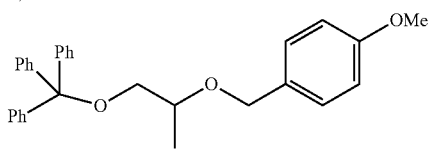

Chemical Formula: C$_{30}$H$_{30}$O$_3$
Molecular Weight: 438.56
C, 82.16; H, 6.89; O, 10.94

The trityl ether (99.82 g, 313.5 mmol) was converted into the orthogonally protected bis ether. To a <10° C. slurry of 2 equiv of NaH in DMF was added dropwise trityl ether at a rate to control gas evolution. After stirring for 15 minutes at <10° C., p-methoxybenzyl chloride was added via syringe. The mixture was warmed to rt (mildly exothermic) and allowed to stir at rt for 1.5 hours. HPLC analysis indicated complete consumption of starting material. Workup consisted of careful quenching of the mixture with 3 volumes of water and EA extraction. The EA layers were washed with water to remove DMF and dried over Na$_2$SO$_4$ to give a hazy oil (150.95 g).

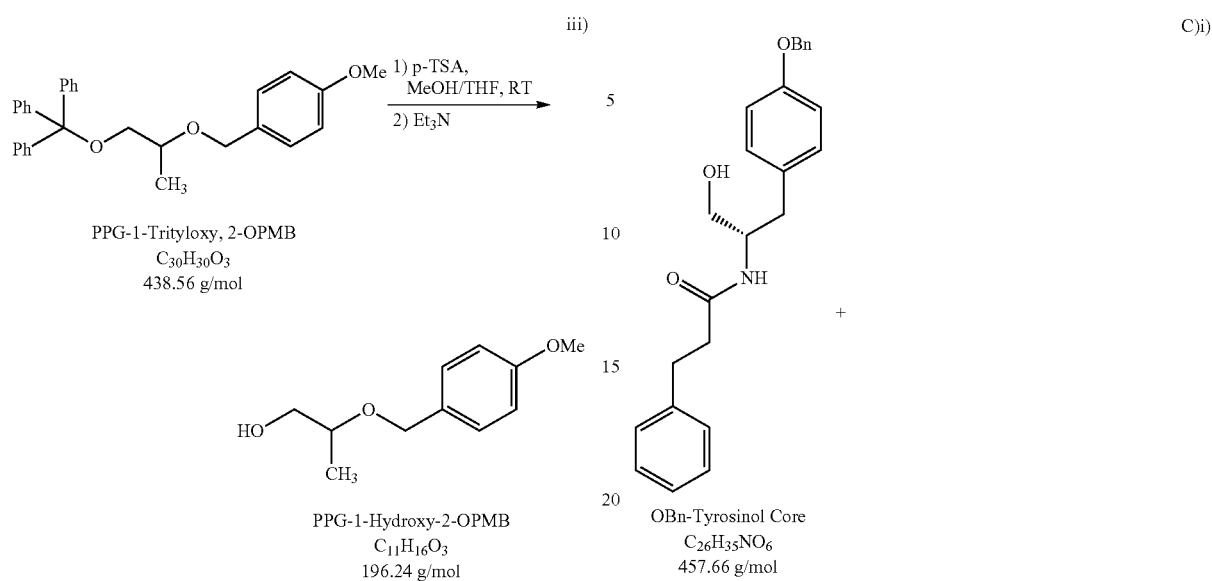

The protected his ether was exposed to a catalytic amount of para-toluenesulfonic acid to detritylate the trityl group. To the protected bis ether (150.95 g, PR030-084-2) in methanol and THF was added a catalytic amount (0.1 eq) of para-toluenesulfonic acid. After 60 minutes at room temperature, thin layer chromatography and HPLC analysis indicated that the reaction was complete. Triethylamine was added to quench the reaction and the solvent was removed via DURP. The desired product was isolated from a silica gel plug to afford 51.74 g (84% yield, Purity=98.4%). $^1$H NMR analysis supported the assigned structure.

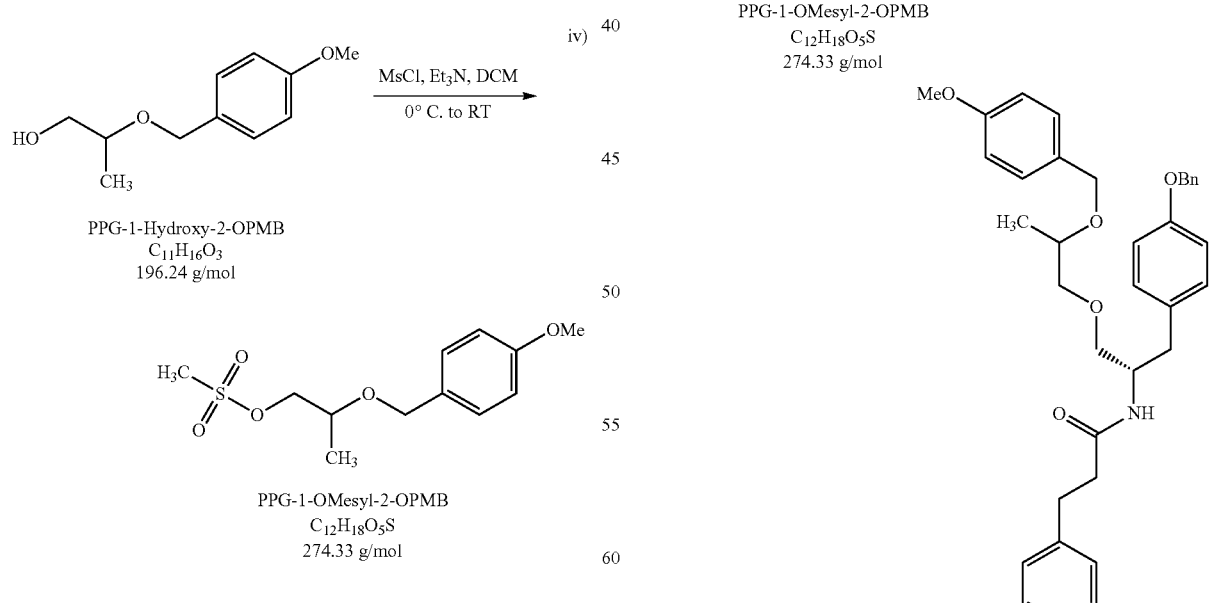

The mesylation of PPG-1-Hydroxy-2-OPMB (20.1 g) was conducted using 2.0 eq of methanesulfonyl chloride and 2.25 eq of triethylamine at <5° C. to give a clean conversion to desired product in 108% crude yield as an oil. This material was sufficiently pure to use for next steps.

20.13 g OBn-Tyrosinol core (from step A) and 2.25 eq PPG-1-OMesyl-2-OPMB (from step B) in DMSO was added 2.0 eq of 1M potassium tert-butoxide (in THF) over 1.6 hours at room temperature. After 15.5 hours at room temperature, 91.9% of desired product had formed and 8.1% of OBn-Tyrosinol core was not fully consumed. An additional 0.3 eq of 1M potassium tert-butoxide was added and the reaction was allowed to stir at 45° C. After an additional 18 hours at 45° C., 98.3% of desired product had formed and 1.7% of OBn-Tyrosinol core was not fully consumed. The reaction mixture was quenched with USP water at room temperature and extracted with ethyl acetate. The combined organic layers were successively washed with USP water, saturated aqueous NaHCO3 solution, brine, and dried over sodium sulfate to afford 39.00 g of an oil. An attempt to recrystallize from toluene/heptane proved to be unsuccessful and provided 25.8 g of solids that were 77.4% pure of desired product.

Celite was added to 25.3 grams of PR030-114-12 dissolved in hot MTBE/Heptane (1:1). This mixture was filtered hot over a bed of Celite. The filtrate was cooled to room temperature and the solids were collected via vacuum filtration to provide 13.1 g of white solids (52.4% yield). A second crop was obtained giving an additional 2.75 g of white solids (an additional 11% yield). The purity of these two crops was 98.8% and 98.1%, respectively. 1H NMR and Mass spec analysis supported the assigned structure for desired product. The combined yield was 63.5%.

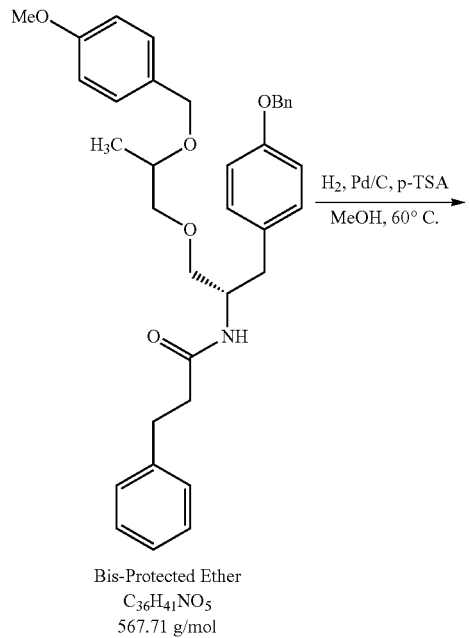

The bis-protected ether (15.7 g) was exposed to one-pot hydrogenation-debenzylation conditions (10% loading of 10% Pd/C and 0.25 eq of p-toluenesulfonic acid) in methanol. After 2 hours at 60° C. under a hydrogen atmosphere, HPLC analysis indicated that the hydrogenation of the benzyl and the debenzylation of PMB ring was complete. The reaction mixture was filtered over Celite and concentrated under reduced pressure. The residue was dissolve in ethyl acetate and a saturated aqueous sodium bicarbonate treatment was conducted to effectively remove p-toluenesulfonic acid, then DURP to provide 12.13 g of an oil (PR030-120-4). Desired product was isolated from an EA/Heptane recrystallization to provide 8.83 g of a white solid (PR030-120-6, 89.4% yield). The purity of PR030-120-6 was 99.3% via HPLC analysis. 1H NMR and Mass spec analysis supported the assigned structure for desired product.

Synthesis 2: Compound 1

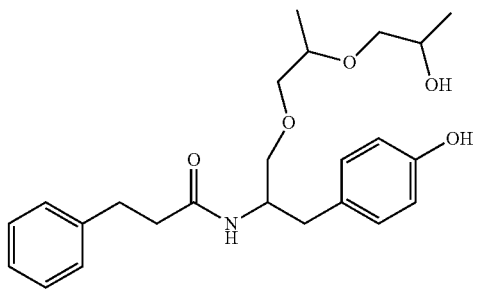 [SMILES: CC(O)COC(C)COCC(Cc1ccc(O)cc1)NC(=O)CCc1ccccc1]

Compound 1 has the structure of general formula IV, with R=PPG and n=2. MW=413

Compound 1 was prepared using the same procedure as described above in Synthesis 1, with the substitution of the PPG, n=1 for PPG, n=2.

It will be understood that the procedures of Synthesis 1 can therefore be applied to produce compounds of formula VII in which Z is PPG. Alternative compounds falling within formula I can be produced by substitution of L-tyrosinol in step (A) with the appropriate amino alcohol (e.g. phenyl alaninol as produced in synthesis a)).

The procedures of Synthesis 1 can also be adapted as described below in Synthesis 3 so that they result in the production of a compound of formula 1 in which Z is PEG.

Synthesis 3: Compound 3

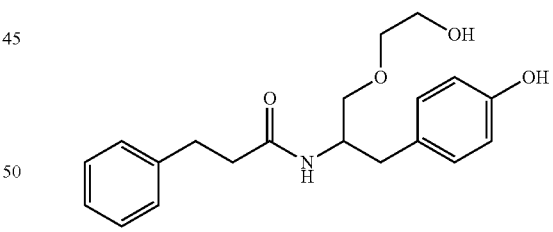

Compound 3 has the structure of general formula IV, with R=PEG and n=1. MW=413

Compound 3 was prepared using the following procedure.

A) Step A was performed as for compound 2.

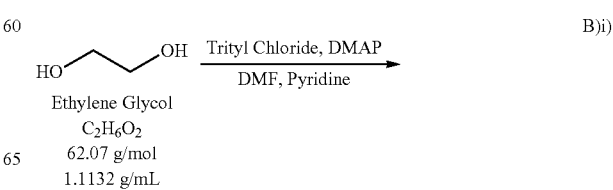

-continued

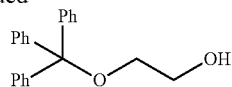

2-(trityloxy)ethanol (Compound A-1)
C$_{21}$H$_{20}$O$_2$
304.38 g/mol

A 5-fold excess of ethylene glycol was treated with trityl-Cl (22.9 g, 82.13 mmol) in the presence of pyridine and DMAP in DMF at rt. The reaction was allowed to stir overnight at room temperature. The mixture was diluted with 3 vol of water and extracted with EA. Isolation of desired product via recrystallization from acetonitrile/water gave 22.87 g of solids (91.5% yield). The purity determined by HPLC was 97.8%. 1H NMR and Mass Spec analysis supported the assigned structure for desired product.

ii)

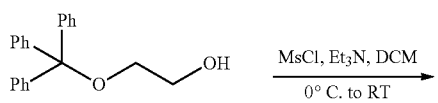

2-(trityloxy)ethanol (Compound A-1)
C$_{21}$H$_{20}$O$_2$
304.38 g/mol

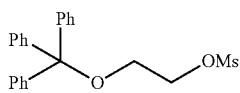

2-(trityloxy)ethanol
methanesulfonate
(Compound B-1)
C$_{22}$H$_{22}$O$_4$S
382.47 g/mol The mesylation of compound A-1 (11.00 g) was conducted using 2.0 eq of methanesulfonyl chloride and 2.25 eq of triethylamine at <5° C. to give a clean conversion to desired product in quantitative yield as a solid (13.85 g). AUC purity=97.5%. Mass spec and $^1$H NMR analysis supported the assigned structure.

C) i) 2.29 g of OBn-Tyrosinol core (from step A) and 2.25 eq of Compound B-1 (from Step B) in DMSO was added 2.0 eq of 1M potassium tert-butoxide (in THF) over 45 mins at room temperature. After 12.25 hours at 35° C., the reaction mixture was quenched with USP water at room temperature and extracted with ethyl acetate. The combined organic layers were successively washed with USP water, saturated aqueous NaHCO$_3$ solution, brine, and dried over sodium sulfate to afford 5.05 g as an oil. This product was purified via column chromatography to isolate the desired product as a solid (2.07 g). AUC purity=97.5%. $^1$H NMR analysis supported the assigned structure for desired product.

ii)

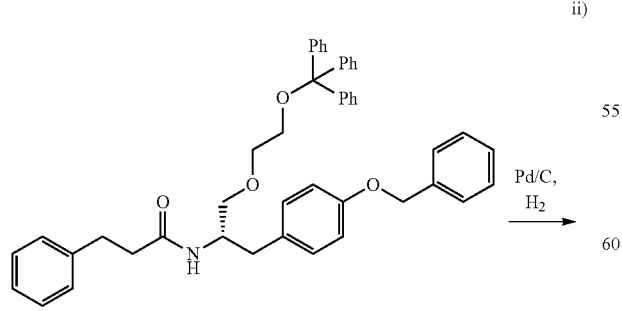

Mol. Wt.: 675.85
AV74S n = 1 Ethylene Glycol
Bis-protected
C-1

-continued

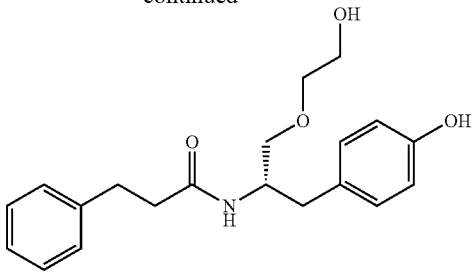

Mol. W.: 343.42
AV74S n = 1 Ethylene Glycol
D-1

2.07 g C-1. C-1 was dissolved in 30 vol methanol at 60 C. 10 wt % Pd/C then 0.25 eq pTSA was added while at 60 C. Hydrogen atmosphere was maintained for 3 hours. The catalyst was removed by hot filtration. The filtrate was DURP to obtain a solid. The solids were dissolved in ethyl acetate and washed with sodium bicarbonate. The organic was dried over sodium sulfate and DURP to give gooey solids.

EXAMPLES

The experiments described below were conducted to demonstrate the utility of compounds of the invention in the treatment of anxiety or depression, using the following compounds.

Compound 1

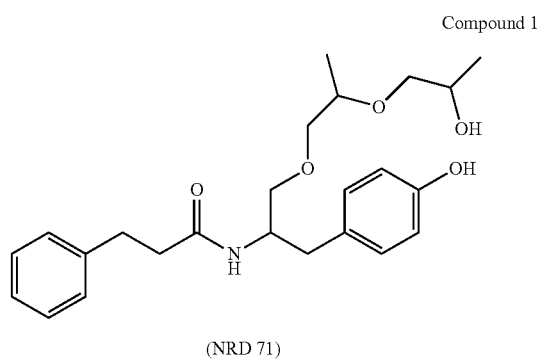

(NRD 71)

Compound 2

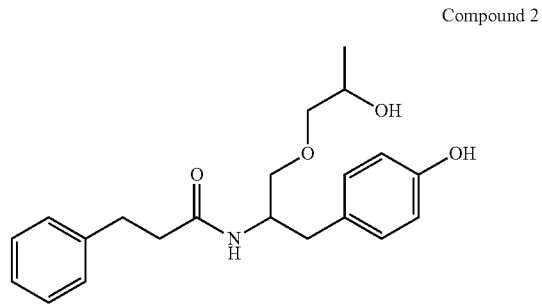

(NRD 135)

Compound 3

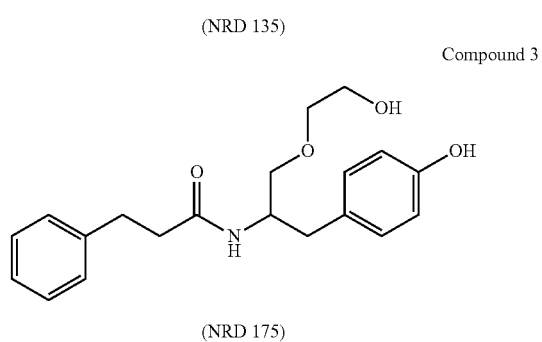

(NRD 175)

Example 1

Open Field Test

Exploratory Locomotor Activity

This method is one of the most popular in evaluation of animals' behaviour. See FIG. 5. It tests both motility parameters and anxiety (Prut et al). An individual mouse is placed in a novel plexiglass arena of 50×50 cm the floor of which is divided into 3 digital zones. The outer peripheral zone 1, the medial zone 2 and the most central zone 3. The animal behaviour in the open field is recorded by videotaping for 20 min and analyzed subsequently digitally using Noldus software for animal behaviour. The measurements include general motility: distance moved, velocity and strong mobility, as well as anxiety parameters including frequency of visits to the central area, time spent in the inner field, and number of rearing events in the centre. The more the animal stays and performs in the centre, it is less anxious.

This method was used to assess the anxiolytic effect of the compounds of the present invention, as follows.

40, 9 week old naïve male Balb/c mice were divided in 5 groups (8 mice in each group) and treated daily (0 min, p.o.) for two weeks, as follows:
1. Control—0.5% DMSO 0.3 ml/mouse, po (3 ml/10 mice) (15 µl DMSO+2994 µl DDW), n=8.
2. Diclofenac 10 mg/Kg=0.3 mg/0.3 ml/mouse, i.p. (3 ml/10 mice), n=8
3. 135S 0.5 mg/Kg=0.015 mg/0.3 ml/mouse, po (3 ml/10 mice) (135S 0.15 mg (Stock 50 mg/1 ml DMSO) 3 µl+2997 µl DDW), n=8
4. 135S 2.5 mg/kg=0.075 mg/0.3 ml/mouse, po (3 ml/10 mice) (175S 0.75 mg (Stock 50 mg/1 ml DMSO) 15 µl+2985 µl DDW), n=8
5. 135S 0.1 mg/Kg=0.003 mg/0.3 ml/mouse, po (3 ml/10 mice) (135S 0.003 mg (Stock 50 mg/1 ml DMSO) 0.6 µl+2999.4 µl DDW), n=8

Fifteen days after treatment, the five groups of mice listed above were subjected to the open field test for 60 minutes. The activity of the mice was assessed by an EthoVision video track system (Noldus Ltd.) A centre zone ("zone 3"; approximately 16% of the total area), a border area ("zone 1"; an 8 cm wide border around the edge of the arena) and an intermediate zone ("zone 2"; the remaining area) were defined. Quantitative parameters, such as the distance travelled and average speed, were recorded for the centre zone and the entire arena.

An Open Field test measures activity in a novel environment and can be used to assess a combination of locomotor activity, exploratory drive, neophobia, agoraphobia and other aspects of anxiety or fear in mice, as well as motor function. Treatment using a 0.1 mg/kg or 5 mg/kg dose of 135S or 175S compound was compared to the effect of treatment with a control substance (DMSO) or Diclofenac. The mice were placed in the centre of the arena and their activity and behaviour was recorded over a period of 20 minutes in respect of the distance moved (cm), velocity (cm/s), strong mobility and immobility. The ratio of total duration between the inner zones 2 and 3 in comparison to the outer zone 1 was recorded. The total duration in the inner zones 2 and 3 was also determined. The results are displayed within FIG. 1A to FIG. 1F.

It can be seen from FIG. 1A to FIG. 1D that treatment with the compounds 135S and 175S of the invention did not show a significant effect on locomotor activity of the mice (i.e. distance moved, velocity, strong mobility and immobility) in comparison to the control mice.

However, when the ratio of total duration in zones 2 and 3 in comparison to total duration in zone 1 was compared, a significant effect was seen in mice treated with the compounds of the invention. Mice usually have an innate fear of the central area of a brightly lit open field but this conflicts with their desire to explore new environments. Anxious mice naturally tend to prefer staying close to the walls of the open field and anxiety-related behaviour can therefore be measured by the degree to which the rodent avoids the centre of the open field arena. As shown by FIG. 1F, a significant increase in the time spent in zones 2 and 3 was seen for mice treated with 135S and 175S in comparison to control mice. The compounds of the invention therefore exhibit an anxiolytic or anti-anxiety effect because they increased the time the mice spent in the open, central areas of the open field rather than close to the walls.

Example 2

Forced Swim Test

This is one of the most widely used tools for screening antidepressant activity preclinically in an acute test and was first described by Porsolt et al (1977). The test is based on the observation that rats and mice develop an immobile posture when placed in an inescapable cylinder of water. This behavior is considered to be a behavioural despair as opposed to an active form of coping with stressful conditions. An antidepressant will reduce immobility and increase motivated behaviour of the rodent to escape from the despaired conditions. This is evidenced by increase in time of swimming, distance moved, velocity and attempts to climb the walls (strong mobility). FST is considered a good screen tool with good reliability and predictive validity.

The test in male mice (Balb/c Harlan IL) was conducted after 4 days of drug administration (90 min post last drug administration). Round glass cylinders 18 cm diameter and 20 cm depth were used. Water temperature was 24-28° C. Motivated behaviour was defined by immobility, swimming and strong mobility. Immobility in the animals was defined by activity lower than 10% movement of the centre of gravity of the animal. Swimming was defined by the distance and the velocity of the animal, and climbing was related to strong mobility (movement of centre of gravity more than 30%). Animals were dropped to the cylinder for 6 min and scoring was performed in the last 4 min after 2 min of adaptation. All results were analyzed by the Noldus (Holland) system including a camera and software for animal behaviour analyses.

Mice were treated with compound 135S at three different concentrations (0.1 mg/kg, 0.5 mg/kg and 2.5 mg/kg), or with the anti-depressant Fluoxetine (10 mg/kg) administered orally in a daily dose for 14 days. The forced swim test was performed on day 1.

In a first trial, the mice were placed in a tank of water, from which they could not escape. The mobility and immobility of the mice was monitored. In a second trial, the same mice were placed back into the tank. The mobility and immobility of the mice was again monitored. The results are displayed in FIG. 2A to FIG. 2C.

The results of FIG. 2A to FIG. 2C show that treatment with 135S leads to an increase in mobility and a decrease in immobility in comparison to control mice and therefore that 135S demonstrates an anti-depressant effect. The effect seen is also greater than that resulting from treatment of mice with the common anti-depressant drug Fluoxetine.

Example 3

Elevated Plus Maze

This model uses the natural fear of rodents to avoid open and elevated places. The apparatus consists of a plus-maze with two enclosed and two opposite open arms, elevated above the floor. Naive animals spend only about 30% of the test time on open arms, while treatment with BDZs significantly increases open-arm exploration (Pellow et al). This is one of the most widely used models to study effects of anxiety-like behaviour. The maze consisted of two opposing open arms (40×10 cm) and two opposing closed arms (40×10 cm, with 40 cm walls) on a platform 50 cm above the ground. The maze is based on aversion of open spaces and therefore restriction of movement to the enclosed arms is expected in mice demonstrating anxiety.

The groups of mice were treated as in Example 2 and an elevated plus maze test was carried out on day 8. This test was used as a further test of the anxiolytic effect of the drugs of the invention.

The mice were placed in the centre of the maze facing an open arm and were allowed to freely explore the maze for 15 minutes. During this time, their behaviour was observed. The results are shown in FIG. 3A to FIG. 3D and show that treatment of the mice with the compound 135S resulted in increased exploration of the maze and increased time spent within the open arms in comparison to control mice. The treated mice therefore exhibited less anxiety than the control mice and this study provides further evidence of the anxiolytic properties of the compounds of the present invention.

Example 4

Marble Burying Test

The marble burying test is a useful model of neophobia, anxiety and obsessive-compulsive behaviour. It has also been proposed that the test may have predictive validity for the screening of novel antidepressants, anxiolytics and antipsychotics. Mice can be expected to bury roughly 75% of the marbles in a 30 min period, although it varies with strain and gender. In this study, male Balb/c mice were used.

The groups of mice were treated as in Example 2 and a marble burying test was carried out on day 15. The mice were placed individually into a cage containing 20 glass marbles and exposed for 20 minutes. The number of marbles buried by the mice was monitored. The results are displayed in FIG. 4 which shows that mice treated with compound 135S buried significantly less marbles than control mice. This test provides further evidence of the anxiolytic properties of this compound, in particular with respect to treatment of obsessive compulsive disorder (OCD).

The invention claimed is:

1. A method for treating anxiety or depression in a human or non-human animal patient in need thereof, which method comprises administering to said patient a therapeutic effective amount of at least one compound or a pharmaceutical composition of:

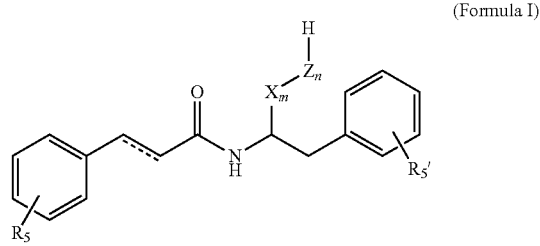

(Formula I)

or a pharmaceutically acceptable salt or hydrate thereof; wherein the dotted line in Formula I represents a single or a double bond; and $R_5$ and $R_5'$ are independently —H, —OH or —$OR_6$, where $R_6$ is a linear or branched $C_1$-$C_4$ alkyl; X is —$CH_2O$—; Z is —$CH_2CH_2O$—, —$CH(CH_3)CH_2O$—, or —$CH_2CH(CH_3)O$—; m is 1; and n is an integer of 1-3.

2. The method as claimed in claim 1, wherein a daily dose of 1.0 mg to 15 g of said compound or said pharmaceutically acceptable salt or hydrate thereof is administered.

3. The method as claimed in claim 1, wherein said compound or said pharmaceutically acceptable salt or hydrate thereof, or said pharmaceutical composition of a compound of Formula I or said pharmaceutically acceptable salt or hydrate thereof, is administered orally.

4. The method according to claim 1, wherein Z is —$CH_2CH(CH_3)O$—.

5. The method according to claim 4, wherein said compound is represented by Formula III:

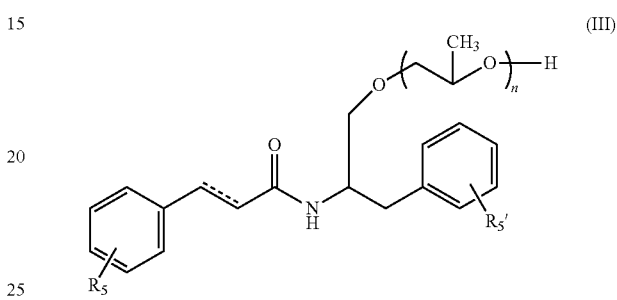

(III)

in which n, $R_5$ and $R_5'$ are as defined in claim 1.

6. The method according to claim 5, wherein $R_5$ is H or OH.

7. The method according to claim 5, wherein $R_5'$ is H or OH.

8. The method according to claim 5, wherein n is an integer of 1-2.

9. The method according to claim 1, which compound is represented by Formula IV, V, VI or VII:

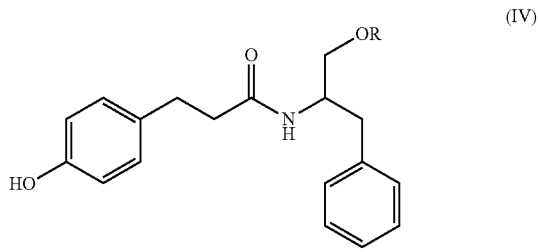

(IV)

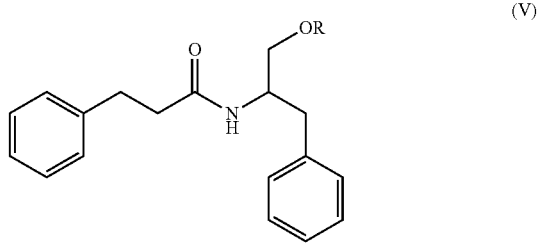

(V)

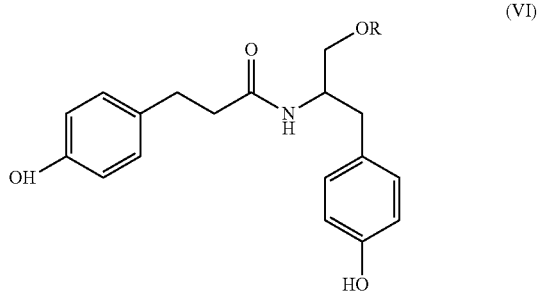

(VI)

-continued

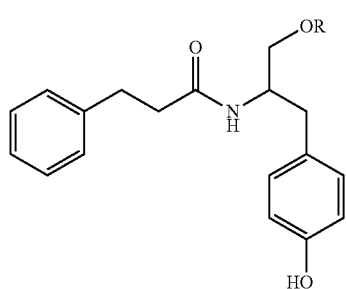

(VII)

in which R is a polyalkylene glycol polymer having n units, wherein n is an integer of 1-3.

10. The method according to claim 1, wherein the compound is a pharmaceutically acceptable salt or hydrate of the compound of Formula (IV), (V), (VI), or (VII), in which R is a polyalkylene glycol polymer having n units, wherein n is an integer of 1-3.

11. The method according to claim 9 or 10, wherein n is an integer of 1-2.

* * * * *